US008901374B2

(12) United States Patent
Bauer et al.

(10) Patent No.: US 8,901,374 B2
(45) Date of Patent: Dec. 2, 2014

(54) FATTY ACID DEHYDRATASES AND USES THEREOF

(75) Inventors: Jörg Bauer, Limburgerhof (DE); Xiao Qiu, Saskatoon (CA); Patricia Vrinten, Saskatoon (CA)

(73) Assignees: BASF Plant Science GmbH, Ludwigshafen (DE); Bioriginal Food & Science Corp., Saskatoon (CA)

( * ) Notice: Subject to any disclaimer, the term of this patent is extended or adjusted under 35 U.S.C. 154(b) by 314 days.

(21) Appl. No.: 12/995,733

(22) PCT Filed: Jun. 2, 2009

(86) PCT No.: PCT/EP2009/056725
§ 371 (c)(1),
(2), (4) Date: Dec. 2, 2010

(87) PCT Pub. No.: WO2009/147127
PCT Pub. Date: Dec. 10, 2009

(65) Prior Publication Data
US 2011/0088123 A1 Apr. 14, 2011

(30) Foreign Application Priority Data

Jun. 3, 2008 (EP) .................................. 08157468

(51) Int. Cl.
*A01H 1/00* (2006.01)
*A01H 5/10* (2006.01)
*C07H 21/04* (2006.01)
*C12P 7/64* (2006.01)
*C12P 21/04* (2006.01)
*C12P 21/06* (2006.01)
*C12N 5/04* (2006.01)
*C12N 5/10* (2006.01)
*C12N 15/82* (2006.01)
*C12N 9/88* (2006.01)

(52) U.S. Cl.
CPC .............. *C12N 15/8247* (2013.01); *C12N 9/88* (2013.01)
USPC .......... 800/281; 800/295; 800/306; 435/69.1; 435/71.1; 435/134; 435/419; 435/430; 435/468; 536/23.2; 536/23.6; 536/23.7; 536/24.1

(58) Field of Classification Search
None
See application file for complete search history.

(56) References Cited

U.S. PATENT DOCUMENTS

2004/0137466 A1 7/2004 Jofuku et al.
2007/0214517 A1 9/2007 Alexandrov et al.

FOREIGN PATENT DOCUMENTS

| CA | 2559360 A1 | 9/2005 | |
| CA | 2573972 A1 * | 1/2006 | ............... A01H 5/00 |
| WO | WO-2005/052162 A1 | 6/2005 | |
| WO | WO-2005/083093 A2 | 9/2005 | |

OTHER PUBLICATIONS

Zhang et al Apr. 2008 Genbank: ACC78512.*
Kihara et al 2008 Journal of Biological Chemistry 283:17 p. 11199-11209.*
Da Costa et al 2006 The Plant Cell 18: p. 1426-1437.*
Bach et al 2008 PNAS 105:38 p. 14727-14731.*
Denic, V., et al., "A Molecular Caliper Mechanism for Determining Very Long-Chain Fatty Acid Length", Cell, 2007, vol. 130, No. 4, pp. 663-677.
Bellec, Y., et al., "Pasticcino2 is a Protein Tyrosine Phosphatase-Like Involved in Cell Proliferation and Differentiation in *Arabidopsis*", Plant J., 2002, vol. 32, No. 5, pp. 713-722.
Joubès, J., et al., "The VLCFA Elongase Gene Family in *Arabidopsis thaliana*: Phylogenetic Analysis, 3D Modelling and Expression Profiling", Plant Mol. Biol., 2008, vol. 67, No. 5, pp. 547-566.
Bach, L., "The Very-Long-Chain Hydroxy Fatty Acyl-CoA Dehydratase PASTICCINO2 is Essential and Limiting for Plant Development", Proc. Natl. Acad. Sci. U. S. A., 2008, vol. 105, No. 38, pp. 14727-14731.
"SubName: Full=Protein Tyrosine Phosphatase, Putative", UniProt Database Accession No. Q4CTD5, Sep. 13, 2005.
"BN18DYSC_UP_129_B08_1APR2008_062 BN18DYSC *Brassica napus* cDNA 5-, mRNA Sequence", GenBank Database Accession No. FG563794, May 28, 2008.
"ELE00003399 Low Light Non-Normalized Long Fraction *Euglena gracilis* cDNA, mRNA Sequence", GenBank Database Accession No. EC676321, Jun. 29, 2006.
"SubName: Full=Putative Uncharacterized Protein", UniProt Database Accession No. Q54YR9, May 24, 2005.
"63JKCOT5_T3_021_B10_22JAN2005_078 63JKCOT5 *Brassica napus* cDNA 5-, mRNA Sequence", GenBank Database Accession No. DY021665, May 15, 2006.
Arondel, V., et al., "Map-Based Cloning of a Gene Controlling Omega-3 Fatty Acid Desaturation in *Arabidopsis*", Science, 1992, vol. 258, pp. 1353-1355.
Broadwater, J. A., et al., "Desaturation and Hydroxylation: Residues 148 and 324 of *Arabidopsis* FAD2, in Addition to Substrate Chain Length, Exert a Major Influence in Partitioning of Catalytic Specificity", The Journal of Biological Chemistry, 2002, vol. 277, No, 18, pp. 15613-15620.

(Continued)

*Primary Examiner* — Brent T Page
*Assistant Examiner* — Matthew Keogh
(74) *Attorney, Agent, or Firm* — Drinker Biddle & Reath LLP

(57) ABSTRACT

The invention provides isolated nucleic acid molecules which encode novel fatty acid dehydratase family members. The invention also provides recombinant expression vectors containing dehydratase nucleic acid molecules, host cells into which the expression vectors have been introduced, and methods for large-scale production of long chain polyunsaturated fatty acids (LCPUFAs), e.g., SDA, EPA and DHA.

30 Claims, 7 Drawing Sheets

(56) References Cited

OTHER PUBLICATIONS

Broun, P., et al., "Catalytic Plasticity of Fatty Acid Modification Enzymes Underlying Chemical Diversity of Plant Lipids", Science, 1998, vol. 282, pp. 1315-1317.

Calvo, A. M., et al., "Genetic Connection Between Fatty Acid Metabolism and Sporulation in *Aspergillus nidulans*", The Journal of Biological Chemistry, 2001, vol. 276, No. 28, pp. 25766-25774.

Crawford, M. A., et al., "Are Deficits of Arachidonic and Docosahexaenoic Acids Responsible for the Neural and Vascular Complications of Preterm Babies?", Am. J. Clin. Nutr., 1997, vol. 66 (suppl), pp. 1032S-1041S.

Giusto, N. M., et al., "Lipid Metabolism in Vertebrate Retinal Rod Outer Segments", Progress in Lipid Research, 2000, vol. 39, pp. 315-391.

Horrocks, L. A., et al., "Health Benefits of Docosahexaenoic Acid (DHA)", Pharmacological Research, 1999, vol. 40, No. 3, pp. 211-215.

Knutzon, D. S., et al., "Identification of Δ5-Desaturase from *Mortierella alpina* by Heterologous Expression in Bakers' Yeast and Canola", J. Biol. Chem., 1998, vol. 273, No. 45, pp. 29360-29366.

Mantle, P. G., et al., "Differentiation of *Claviceps purpurea* in Axenic Culture", J. Gen. Microbiol., 1976, vol. 93, pp. 321-334.

Martinez, M., "Tissue Levels of Polyunsaturated Fatty Acids During Early Human Development," J. Pediatr., 1992, vol. 120, pp. S129-S138.

Mey, G., et al., "The Biotrophic, Non-Appressorium-Forming Grass Pathogen *Claviceps purpurea* Needs a *Fus3/Pmk1* Homologous Mitogen-Activated Protein Kinase for Colonization of Rye Ovarian Tissue", Mol. Plant Microbe Interact., 2002, vol. 15, No. 4, pp. 303-312.

Okuley, J., et al., "*Arabidopsis FAD2* Gene Encodes the Enzyme That is Essential for Polyunsaturated Lipid Synthesis", The Plant Cell, 1994, vol. 6, pp. 147-158.

Qi, B., et al., "Production of Very Long Chain Polyunsaturated Omega-3 and Omega-6 Fatty Acids in Plants", Nat. Biotech., 2004, vol. 22, No. 6, pp. 739-745.

Shanklin, J., et al., "Desaturation and Related Modifications of Fatty Acids", Annu. Rev. Plant Physiol. Plant Mol. Biol., 1998, vol. 49, pp. 611-641.

Spector, A. A., "Essentiality of Fatty Acids," Lipids, 1999, vol. 34 (Supplement), pp. S1-S3.

Sperling, P., et al., "The Evolution of Desaturases," Prostaglandins, Leukotrienes and Essential Fatty Acids, 2003, vol. 68, pp. 73-95.

Tudzynski, P., et al., "Biotechnology and Genetics of Ergot Alkaloids," Appl. Microbiol. Biotechnol., 2001, vol. 57, pp. 593-605.

\* cited by examiner

Figure 1: Alignment of Dehydratase sequences from Brassica napus of the (A) cDNA sequences of mRNA (SEQ ID NO: 1 and 3), (B) translated amino acid sequences (SEQ ID NO: 2 and 4).

A)

```
              *          20          *          40          *
BN-7   : GTTAGTACATGGCGGGGTCTTTCTCCTTCGTCCGTCGCGTGTACCTCACT : 50
BN-G6  : GTTAGTACATGGCGGGGTCTTTCTCCTTCGTTCGTCGCGTGTACCTCACT : 50

60         *          80          *         100
BN-7   : CTCTACAATTGGATCGTCTTTGCAGGATGGGATCAAGTTCTGTACTTTGC : 100
BN-G6  : CTCTACAATTGGATCGTCTTTGCAGGATGGGGTCAAGTTCTGTACTTTGC : 100

*         120          *         140          *
BN-7   : GGTAAAGACGTTGAAGGAAACTGGACATGAACATGTCTATGACGCAGTCG : 150
BN-G6  : GGTAAAGACGTTGAAGGAAAGTGGACATGAAGATGTTTATGACGCTGTTG : 150

160          *         180          *         200
BN-7   : AGAAGCCTCTCCAGCTTGCTCAGACCGCCGCCGTTCTCGAGATTCTACAT : 200
BN-G6  : AGAAGCCTCTCCAGCTTGCTCAGACCGCCGCCGTTCTCGAGATTCTTCAT : 200

*         220          *         240          *
BN-7   : GGACTAGTTGGTTTGGTTAGATCTCCTGTTTTCAGCAACTCTGCCGCAGAT : 250
BN-G6  : GGATTAGTAGGTTTGGTGAGATCTCCTGTCTCGCAACTCTGCCGCAGAT : 250

260          *         280          *         300
BN-7   : AGGTTCAAGGCTGTTTCTAACTTGGGCAATCCTATACAGCTTTCCAGAGG : 300
BN-G6  : AGGTTCAAGGCTGTTTCTCACTTGGGCCATCCTATACAGCTTTCCAGAGG : 300

*         320          *         340          *
BN-7   : TCCAGCCACATTTTCTTGTTGCTTCGCTGGTCATAAGCTGGTCTATCACC : 350
BN-G6  : TCCAGGCACATTTTCTTGTTGCGTCGCTGGTCATAAGCTGGTCTATCACG : 350

360          *         380          *         400
BN-7   : GAGATTATTCGCTACTCCTTCTTTGGTCTCAAGGAAGCTCTAGGCTTTGC : 400
BN-G6  : GAGATTATTCGCTACTCCTTCTTTGGTCTGAAGGAAGCTGTAGGCTTTGC : 400

*         420          *         440          *
BN-7   : ACCTTCATGGCACTTGTGGCTCAGATACAGCAGCTTTTAGTGCTCTACC : 450
BN-G6  : ACCTTCATGGCACTTGTGGCTCAGATACAGCAGCTTTTAGTGCTATACC : 450
```

Figure 1 (Continued)

```
              460         *         480         *         500
BN-7  : CGACCGGTATCACCAGTGAAGTAGGTCTTATCTACCTTGCGTTACCACAC : 500
BN-G6 : CAACCGGTATCACCAGTGAAGTAGGTCTTATCTACCTTGCGTTACCACAC : 500

*         520         *         540         *
BN-7  : ATCAAGACGTCTGAGATGTACAGCGTTAGGATGCCAAACACATTGAACTT : 550
BN-G6 : ATCAAGACGTCTGAGATGTACAGTGTTAGGATGCCGAACACATTGAACTT : 550

560         *         580         *         600
BN-7  : CTCATTCGACTTCTTCTACGCAACGATACTCGCCCTTGCAATATATGTCC : 600
BN-G6 : CTCATTCGACTTCTTCTACGCAACGTTACTCGTCCTTGCAATATATGTCC : 600

*         620         *         640         *
BN-7  : CAGGCAGTCCACACATGTACAGGTACATGCTTGGTCAGCGTAAGAGAGCT : 650
BN-G6 : CAGGCAGTCCACACATGTACAGGTACATGCTTGGTCAGCGTAAGAGAGCT : 650

660         *
BN-7  : CTCTCCAAATCCAAGAGGGAATAAAAA : 677
BN-G6 : CTCTCCAAATCCAAGAGGGAATAAAAA : 677
```

B)

```
                *         20         *         40         *
BN-7  : MAGSFSFVRRVYLTLYNWIVFAGWDQVLYFAVKTLKESGHENVYDAVEKP : 50
BN-G6 : MAGSFSFVRRVYLTLYNWIVFAGWAQVLYFAVKTLKETGHEIVYDAVEKP : 50

60         *         80         *         100
BN-7  : LQLAQTAAVLEILHGLVGLVRSPVSATLPQIGSRLFLTWGILYSFPEVQT : 100
BN-G6 : LQLAQTAAVLEILHGLVGLVRSPVSATLPQIGSRLFLTWGILYSFPEVQS : 100

*         120         *         140         *
BN-7  : HFLVASLVISWSITEIIRYSFFGLKEALGFAPSWHLWLRYSSFLVLYPTG : 150
BN-G6 : HFLVASLVISWSITEIIRYSFFGLKEALGFAPSWHLWLRYSSFLVLYPTG : 150

160         *         180         *         200
BN-7  : ITSEVGLIYLALPHIKTSEMYSVRMPNTLNFSFDFFYATILALAIYVPGS : 200
BN-G6 : ITSEVGLIYLALPHIKTSEMYSVRMPNTLNFSFDFFYATLLVLAIYVPGS : 200

*         220
BN-7  : PHMYRYMLGQRKRALSKSKRE- : 221
BN-G6 : PHMYRYMLGQRKRALSKSKRE- : 221
```

Figure 2: Alignment of Dehydratase sequences from Euglena gracilis of the (A) cDNA sequences of mRNA (SEQ ID NO: 5, 7 and 9), (B) translated amino acid sequences (SEQ ID NO: 6, 8 and 10).

A)

```
                       *        20         *        40         *
EG-FF4 : ---------------------------------------------------- :   -
EG-L3  : GGAACATGCACCACTTTCGGCCGATCGAGGTGTTTGAGCAGGAAACGTCC   :  50
EG-S6  : ---------------------------------------------------- :   -

60         *        80         *       100
EG-FF4 : ---------------------------------------------------- :   -
EG-L3  : AGCGCGGTGATGGGCCTCCTCCTGATCAATGACATCAAGAACGAGAACAG   : 100
EG-S6  : ---------------------------------------------------- :   -

*       120         *       140         *
EG-FF4 : ---------------------------------------------------- :   -
EG-L3  : TGTTGCTAATCCAGCCACCCCACTCCGCAATCCATTGCTGCTGTTCACCG   : 150
EG-S6  : ---------------------------------------------------- :   -

160         *       180         *       200
EG-FF4 : ---------------------------------------------------- :   -
EG-L3  : ACACGTCTTTCCATGGTGGGGCCTGGAGGTGTGGCTTCAAGTTTGGATCC   : 200
EG-S6  : ---------------------------------------------------- :   -

*       220         *       240         *
EG-FF4 : ----------------GGAAGATG                             :  34
EG-L3  : ATTGGTGTGGGGTCCGTCCTTTCC                             : 250
EG-S6  : ---------------------------------------------------- :   -

260         *       280         *       300
EG-FF4 :          ATGTACAACGCTGGCCAAGCTGGCGGTTGGATGATTG        :  84
EG-L3  :          ATGTACAACGCTGGCCAAGCTGGCGGTTGGATGATTG        : 300
EG-S6  : --------GGAACATGTACAACGCTGGCCAAGCTGGCGGTTGGATGATTG    :  42

*       320         *       340         *
EG-FF4 : CCCTGGGGAAGATCCTGGCTCATGCCGCCTCCGGCAACAAGTCCTCCCTG   : 134
EG-L3  : CCCTGGGGAAGATCCTGGCTCATGCCGCCTCCGGCAACAAGTCCTCCCTG   : 350
EG-S6  : CCCTGGGGAAGATCCTGGCTCATGCCGCCTCCGGCAACAAGTCCTCCCTG   :  92

360         *       380         *       400
EG-FF4 : TGGGGAGCGGTGGGGCCGACCATCAGCAAGTTCCAGTGGCTGGCCGTTCT   : 184
EG-L3  : TGGGGAGCGGTGGGGCCGACCATCAGCAAGTTCCAGTGGCTGGCCGTTCT   : 400
EG-S6  : TGGGGAGCGGTGGGGCCGACCATCAGCAAGTTCCAGTGGCTGGCCGTTCT   : 142
```

Figure 2 (Continued)

```
              *         420         *         440         *
EG-FF4 : GGAGGTGGTCCACGCCGCCGTCGGCATGGTGCGGTCCCCCGTGGCAACCA : 234
EG-L3  : GGAGGTGGTCCACGCCGCCTTCGGCATGGTGCGGTCCCCCGTGGCAACCA : 450
EG-S6  : GGAGGTGGTCCACGCCGCCGTCGGCATGGTGCGGTCCCCCGTGGCAACCA : 192

460       *         480         *         500
EG-FF4 : CCTTCGTGCAGGTCCTGTCGCGCGTGATGCTGGTGAGTGCCGTCCAGTAC : 284
EG-L3  : CCTTCGTGCAGGTCCTGTCGCGCGTGATGCTGGTGAGTGCCGTCCAGTAC : 500
EG-S6  : CCTTCGTGCAGGTCCTGTCGCGCGTGATGCTGGTGAGTGCCGTCCAGTAC : 242

*         520         *         540         *
EG-FF4 : GCCCCGTCCACCCAGGGCAACGACAACTGGTTCTTGTGGCTGATGTGCCT : 334
EG-L3  : GCCCCGTCCACCCAGGGCAACGACAACTGGTTCTTGTGGCTGATGTGCCT : 550
EG-S6  : GCCCCGTCCACCCAGGGCAACGACAACTGGTTCTTGTGGCTGATGTGCCT : 292

560       *         580         *         600
EG-FF4 : GGCCTGGAGCATCACCGAAGTGGTGCGGTACAGCTACTACAGCCTGAGCC : 384
EG-L3  : GGCCTGGAGCATCACCGAAGTGGTGCGGTACAGCTACTACAGCCTGAGCC : 600
EG-S6  : GGCCTGGAGCATCACCGAAGTGGTGCGGTACAGCTACTACAGCCTGAGCC : 342

*         620         *         640         *
EG-FF4 : AGCAGGGGGTCAATGACAAGCTGCTCACGTGGTTGCGGTACAGCCTGTTC : 434
EG-L3  : AGCAGGGGGTCAATGACAAGCTGCTCACGTGGTTGCGGTACAGCCTGTTC : 650
EG-S6  : AGCAGGGGGTCAATGACAAGCTGCTCACGTGGTTGCGGTACAGCCTGTTC : 392

660       *         680         *         700
EG-FF4 : GTGGTGCTGTACCCTGCCGGGGTGGCCGGGGAAATGGGCTGCCTGTACAA : 484
EG-L3  : GTGGTGCTGTACCCTGCCGGGGTGGCCGGGGAAATGGGCTGCCTGTACAA : 700
EG-S6  : GTGGTGCTGTACCCTGCCGGGGTGGCCGGGGAAATGGGCTGCCTGTACAA : 442

*         720         *         740         *
EG-FF4 : GTCCATCCCCGCCATGAAGGACACCCCCCCGGCAGACGCCCCCTTCCTTG : 534
EG-L3  : GTCCATCCCCGCCATGAAGGACACCCCCCCGGCAGACGCCCCCTTCCTTG : 750
EG-S6  : GTCCATCCCCGCCATGAAGGACACCCCCCCGGCAGACGCCCCCTTCCTTG : 492

760       *         780         *         800
EG-FF4 : TGAAGCACATGCTGCAGCCAATGCTGAAGAATTCCCTGGGGTACCTGCTC : 584
EG-L3  : TGAAGCACATGCTGCAGCCAATGCTGAAGAATTCCCTGGGGTACCTGCTC : 800
EG-S6  : TGAAGCACATGCTGCAGCCAATGCTGAAGAATTCCCTGGGGTACCTGCTC : 542

*         820         *         840         *
EG-FF4 : ATCGTTGTGCCGGTTTATGTTGTTGGGCTGAAAACTCTGTATTCATACAT : 634
EG-L3  : ATCGTTGTGCCGGTTTATGTTGTTGGGCTGAAAACTCTGTATTCATACAT : 850
EG-S6  : ATCGTTGTGCCGGTTTATGTTGTTGGGCTGAAAACTCTGTATTCATACAT : 592

860       *         880         *         900
EG-FF4 : GCTGGCACAGCGCCGAAAAATCTTTGGTGGTGCCGAGAAGAAGAATCAAT : 684
EG-L3  : GCTGGCACAGCGCCGAAAAATCTTTGGTGGTGCCGAGAAGAAGAATCAAT : 900
EG-S6  : GCTGGCACAGCGCCGAAAAATCTTTGGTGGTGCCGAGAAGAAGAATCAAT : 642

*
EG-FF4 : GACACAAGCTTGG : 697
EG-L3  : GACACAAGCTTGG : 913
EG-S6  : GACACAAGCTTGG : 655
```

```
             *        20         *        40         *
EG-FF4 : -------------------------------------------------- :   -
EG-L3  : MHHFRPIEVFEQETSSAVMGLLLINDIKNENSVANPATPLRNPLLLFTDT :  50
EG-S6  : -------------------------------------------------- :   -

60        *        80         *       100
EG-FF4 : ---------------------M................MYNAGQAGGWMIAL :  28
EG-L3  : SFHGGAWRCGFKFGSIGVGSVLS...............MYNAGQAGGWMIAL : 100
EG-S6  : ---------------------------------------MYNAGQAGGWMIAL :  14

*        120        *        140         *
EG-FF4 : GKILAHAASGNKSSLWGAVGPTISKFQWLAVLEVVHAANGMVRSPVATTF :  78
EG-L3  : GKILAHAASGNKSSLWGAVGPTISKFQWLAVLEVVHAAFGMVRSPVATTF : 150
EG-S6  : GKILAHAASGNKSSLWGAVGPTISKFQWLAVLEVVHAANGMVRSPVATTF :  64

160        *        180         *       200
EG-FF4 : MQVLSRVMLVSAVQYAPSTQGNDNWFLWLMCLAWSITEVVRYSYYSLSQQ : 128
EG-L3  : VQVLSRVMLVSAVQYAPSTQGNDNWFLWLMCLAWSITEVVRYSYYSLSQQ : 200
EG-S6  : MQVLSRVMLVSAVQYAPSTQGNDNWFLWLMCLAWSITEVVRYSYYSLSQQ : 114

*        220        *        240         *
EG-FF4 : GVNDKLLTWLRYSLFVVLYPAGVAGEMGCLYKSIPAMKDTPPADAPFLVK : 178
EG-L3  : GVNDKLLTWLRYSLFVVLYPAGVAGEMGCLYKSIPAMKDTPPADAPFLVK : 250
EG-S6  : GVNDKLLTWLRYSLFVVLYPAGVAGEMGCLYKSIPAMKDTPPADAPFLVK : 164

260        *        280         *
EG-FF4 : HMLQPMLKNSLGYLLIVVPVYVVGLKTLYSYMLAQRRKIFGGAEKKNQ- : 226
EG-L3  : HMLQPMLKNSLGYLLIVVPVYVVGLKTLYSYMLAQRRKIFGGAEKKNQ- : 298
EG-S6  : HMLQPMLKNSLGYLLIVVPVYVVGLKTLYSYMLAQRRKIFGGAEKKNQ- : 212
```

Figure 3: Alignment of the amino acid sequences of dehydratases from Brassica napus (BN-G6, BN-7), Euglena gracilis (EG-L3, EG-FF4, EG-S6) and Saccharomyces cerevisae (YJL097w).

```
                    *         20         *         40         *
BN-7    : --------------------------------------------------  :   -
BN-G6   : --------------------------------------------------  :   -
YJL097w : --------------------------------------------------  :   -
EG-L3   : MHHFRPIEVFEQETSSAVMGLLLINDIKNENSVANPATPLRNPLLLFTDT  :  50
EG-FF4  : --------------------------------------------------  :   -
EG-S6   : --------------------------------------------------  :   -

60         *         80         *        100
BN-7    : ---------------------MAGSFSEVRRV TLYNWIVFAGWDQVL    :  28
BN-G6   : ---------------------MAGSFSEVRRV TLYNWIVFAGWAQVL    :  28
YJL097w : -----------------------MSKKLASPLS DLYNLLSAVGWSYLL   :  27
EG-L3   : SFHGGAWRCGFKFGSIGVGSVLSAVETNYVLKT TMYNAGQAGGWMIAL    : 100
EG-FF4  : ------------------------MAVETNYVLKT TMYNAGQAGGWMIAL :  28
EG-S6   : --------------------------------MYNAGQAGGWMIAL      :  14

*        120         *        140         *
BN-7    : YFAVKTLKESGHEN YD EKP QLAQTAAVLEII GL GLVRSPVSATL   :  78
BN-G6   : YFAVKTLKETGHEH YD EKP QLAQTAAVLEII GL GLVRSPVSATL   :  78
YJL097w : YLVISLYPKVGQPAF YQTKNVASLVQCGAIIEIINSF GVVRSPLLTV    :  77
EG-L3   : GKILAHAASGNKSS WG GPT SKFQWLAVLEVV AAF GMVRSPVATF   : 150
EG-FF4  : GKILAHAASGNKSS WG GPT SKFQWLAVLEVV AA GMVRSPVATF    :  78
EG-S6   : GKILAHAASGNKSS WG GPT SKFQWLAVLEVV AA GMVRSPVATF    :  64

160         *        180         *        200
BN-7    : PQIGSRLFLTWGIL S--FP VQTH L ASLVI SWSITEIIRY FFG K  : 126
BN-G6   : PQIGSRLFLTWGIL S--FP VQSH L ASLVI SWSITEIIRY FFG K  : 126
YJL097w : AQVSSRLEVVLGIFQLLPNTSGVQSVVYISLLAWSITEIVRYLYYFFML   : 127
EG-L3   : VQVLSRVMIVSAVQ AP-ST GNDN F WLMCLAWSITEVVRY YYS S   : 199
EG-FF4  : MQVLSRVMIVSAVQ AP-ST GNDN F WLMCLAWSITEVVRY YYS S   : 127
EG-S6   : MQVLSRVMIVSAVQ AP-ST GNDN F WLMCLAWSITEVVRY YYS S   : 113

*        220         *        240         *
BN-7    : A-L FAPSWHL LRY SF VLYPTGIT SEV LIYLAL H T---EMYS  : 172
BN-G6   : A-L FAPSWHL LRY SF VLYPTGIT SEV LIYLAL H T---EMYS  : 172
YJL097w : VFKNGAPKT ILLRY IF ILYPTGV ASELRII YCAL NAAESQ----- : 170
EG-L3   : --Q VNDKLLT LRY IF VLYPAGV AGEM CLYKSI A D PPADAPF : 247
EG-FF4  : --Q VNDKLLT LRY IF VLYPAGV AGEM CLYKSI A D PPADAPF : 175
EG-S6   : --Q VNDKLLT LRY IF VLYPAGV AGEM CLYKSI A D PPADAPF : 161

260         *        280         *        300
BN-7    : RMPNTLNFSF FFYAT T ALA YVF SPHMYR MLGQRKR ALSKSK E- : 221
BN-G6   : RMPNTLNFSF FFYAT T ALA YVF SPHMYR MLGQRKR ALSKSK E- : 221
YJL097w : ------Y--SLLYKRIL AAMLAYI FF PMLFLHMV QRKK VMKSLRSSF : 212
EG-L3   : VKHMLQPMLK SLGYL VP YVV GLKTLYS ML QRRKI FGGAE KN    : 297
EG-FF4  : VKHMLQPMLK SLGYL VP YVV GLKTLYS ML QRRKI FGGAE KN    : 225
EG-S6   : VKHMLQPMLK SLGYL VP YVV GLKTLYS ML QRRKI FGGAE KN    : 211

BN-7    : -----  :  -
BN-G6   : -----  :  -
YJL097w : GKKLI  : 217
EG-L3   : Q----  : 298
EG-FF4  : Q----  : 226
EG-S6   : Q----  : 212
```

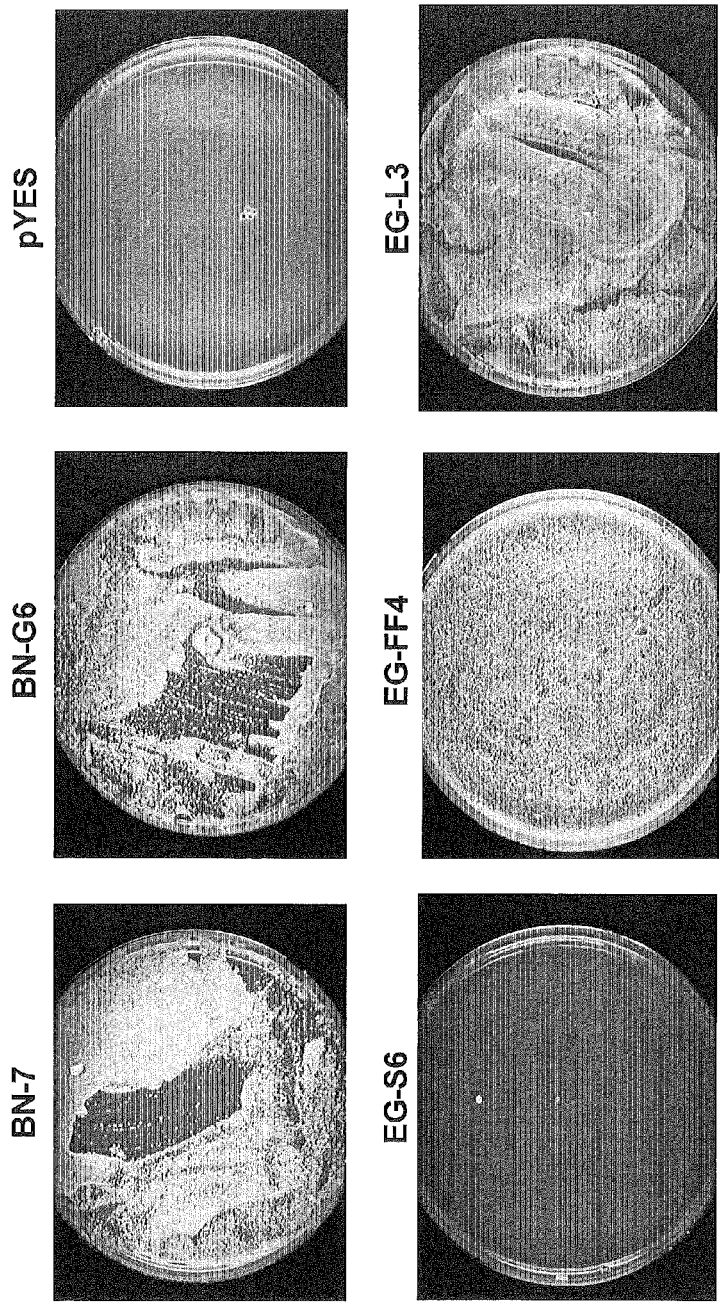

FATTY ACID DEHYDRATASES AND USES THEREOF

RELATED APPLICATIONS

This application is a national stage application (under 35 U.S.C. §371) of PCT/EP2009/056725, filed Jun. 2, 2009, which claims benefit of European application 08157468.3, filed Jun. 3, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00060. The size of the text file is 17 KB, and the text file was created on Dec. 1, 2010.

The invention in principle pertains to the field of recombinant manufacture of fatty acids. It provides nucleic acid molecules which encode novel fatty acid dehydratase family members. The invention also provides recombinant expression vectors containing dehydratase nucleic acid molecules, host cells into which the expression vectors have been introduced, and methods for large-scale production of long chain polyunsaturated fatty acids (LCPUFAs), e.g., ARA, EPA and DHA.

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal dehydratases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of dehydratases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3) and arachidonic acid (C20:4). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032 S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizerns, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and AA are both 45 essential fatty acids. They form a unique class of food and feed constituents for humans and animals. EPA belongs to the n-3 series with five double bonds in the acyl chain. EPA is found in marine food and is abundant in oily fish from North Atlantic. AA belongs to the n-6 series with four double bonds. The lack of a double bond in the ω-3 position confers on AA different properties than those found in EPA. The eicosanoids produced from AA have strong inflammatory and platelet aggregating properties, whereas those derived from EPA have anti-inflammatory and anti-platelet aggregating properties. AA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

The predominant sources of GLA are oils from plants such as evening primrose (*Oenothera biennis*), borage (*Borago officinalis* L.), black currant (*Ribes nigrum*), and from microorganisms such as *Mortierella* sp., *Mucor* sp., and Cyanobacteria. However, use of these GLA sources is not ideal due to large fluctuations in availability and costs associated with extraction processes.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as GLA, DHA, EPA and AA.

Therefore, the technical problem underlying the present invention could be seen as the provision of means and methods for complying with the aforementioned needs. It is solved by the embodiments characterized in the claims and herein below.

Accordingly, the present invention relates to a nucleic acid molecule comprising a nucleic acid sequence selected from the group consisting of:

a) a nucleic acid sequence encoding a fatty acid dehydratase from *Brassica napus* or *Euglena gracilis*;

b) a nucleic acid sequence comprising a sequence as shown in SEQ ID NO:1, 3, 5, 7 or 9;

c) a nucleic acid sequence encoding a polypeptide comprising the amino acid sequence as shown in SEQ ID NO:2, 4, 6, 8 or 10;

d) a nucleic acid sequence encoding a naturally occurring allelic variant of a polypeptide comprising the amino acid sequence as shown in SEQ ID NO: 2, 4, 6, 8 or 10;

e) a nucleic acid sequence encoding a polypeptide being at least 50% identical to the amino acid sequence shown in SEQ ID NO: 2, 4, 6, 8 or 10, wherein said nucleic acid sequence encodes a polypeptide having dehydratase activity;

f) a nucleic acid sequence which is at least 50% identical to the nucleic acid sequence of any one of a) to e), wherein said nucleic acid sequence encodes a polypeptide having dehydratase activity;

g) a nucleic acid sequence which hybridizes to the nucleic acid sequence of any one of a) to e) under stringent conditions, wherein said nucleic acid sequence encodes a polypeptide having dehydratase activity; and h) a nucleic acid sequence of at least 15 contiguous nucleotides of the entire nucleotide sequence of SEQ ID NO:1, 3, 5, 7 or 9.

Preferably, the nucleic acid molecule of the present invention encodes a fatty acid dehydratase protein having an activity of catalyzing the removal of $H_2O$ from 3-hydroxyacyl fatty acid. More preferably, the hydroxyl-group ist at position $\Delta 3$ of the fatty acid.

The term "nucleic acid molecule" as used in accordance with the present invention further encompasses variants of the aforementioned specific nucleic acid molecules, i.e. those shown in SEQ ID NO: 1, 3, 5, 7 or 9 or those encoding a polypeptide having an amino acid sequence as shown in SEQ ID NO: 2, 4, 6, 8 or 10. Said variants may represent orthologs, paralogs or other homologs of the polynucleotide of the present invention.

The nucleic acid molecule variants, preferably, also comprise a nucleic acid sequence characterized in that the sequence can be derived from the aforementioned specific nucleic acid sequences shown in SEQ ID NO: 1, 3, 5, 7 or 9 by at least one nucleotide substitution, addition and/or deletion whereby the variant nucleic acid sequence shall still encode a polypeptide having dehydratase activity as specified above. Variants also encompass nucleic acid molecules comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 65° C., preferably, followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, nucleic acid molecule variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the nucleic acid molecule or the amino acid sequence of the polypeptide of the present invention with other dehydratase sequences. Oligonucleotides suitable as PCR primers as well as suitable PCR conditions are described in the accompanying Examples. As a template, DNA or cDNA from bacteria, fungi, plants or animals may be used. Further, variants include nucleic acid molecule comprising nucleic acid sequences which are at least 50%, at least 60%, at least 70%, at least 75%, at least 80%, at least 85%, at least 90%, at least 95%, at least 98% or at least 99% identical to the nucleic acid sequences shown in SEQ ID NO: 1, 3, 5, 7 or 9 retaining dehydratase activity. Moreover, also encompassed are nucleic acid molecule which comprise nucleic acid sequences encoding amino acid sequences which are at least 50%, at least 60%, at least 70%, at least 75%, at least 80%, at least 85%, at least 90%, at least 95%, at least 98% or at least 99% identical to the amino acid sequences shown in SEQ ID NO: 2, 4, 6, 8 or 10 wherein the polypeptide comprising the amino acid sequence retains dehydratase activity. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A nucleic acid molecule comprising a fragment of any of the aforementioned nucleic acid sequences is also encompassed as a nucleic acid molecule of the present invention. The fragment shall encode a polypeptide which still has dehydratase activity as specified above. Accordingly, the polypeptide may comprise or consist of the domains of the polypeptide of the present invention conferring the said biological activity. A fragment as meant herein, preferably, comprises at least 15, at least 20, at least 50, at least 100, at least 250 or at least 500 consecutive nucleotides of any one of the aforementioned nucleic acid sequences or encodes an amino acid sequence comprising at least 5, at least 10, at least 20, at least 30, at least 50, at least 80, at least 100 or at least 150 consecutive amino acids of any one of the aforementioned amino acid sequences.

The variant nucleic acid molecule or fragments referred to above, preferably, encode polypeptides retaining at least 10%, at least 20%, at least 30%, at least 40%, at least 50%, at least 60%, at least 70%, at least 80% or at least 90% of the dehydratase activity exhibited by the polypeptide shown in SEQ ID NO: 2, 4, 6, 8 or 10. The activity may be tested as described in the accompanying Examples.

The nucleic acid molecules of the present invention either essentially consist of the aforementioned nucleic acid sequences or comprise the aforementioned nucleic acid sequences. Thus, they may contain further nucleic acid sequences as well. Preferably, the nucleic acid molecule of the present invention may comprise further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the nucleic acid molecule of the present invention may encode fusion proteins wherein one partner of the fusion protein is a polypeptide being encoded by a nucleic acid sequence recited above and the other partner of the fusion protein is a heterologous polypeptide. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Variant nucleic acid molecules as referred to in accordance with the present invention may be obtained by various natural as well as artificial sources. For example, nucleic acid molecules may be obtained by in vitro and in vivo mutagenesis approaches using the above mentioned specific nucleic acid molecules as a basis. Moreover, nucleic acid molecules being homologs or orthologs may be obtained from various animal, plant or fungus species. Preferably, they are obtained from plants such as algae, for example *Isochrysis, Mantoniella, Ostreococcus* or *Crypthecodinium*, algae/diatoms such as *Phaeodactylum* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from Euteleostomi, Actinopterygii; Neopterygii; Teleostei; Euteleostei, Protacanthopterygii, Salmoniformes; Salmonidae or Oncorhynchus, more preferably, from the order of the Salmoniformes, most preferably, the family of the Salmonidae, such as the genus *Salmo*, for example from the genera and species *Oncorhynchus mykiss, Trutta trutta* or *Salmo trutta* fario. Moreover, the nucleic acid molecules may be obtained from the diatoms such as the genera *Thallasiosira* or *Crypthecodinium*.

The nucleic acid molecule of the present invention shall be provided, preferably, either as an isolated nucleic acid molecule (i.e. isolated from its natural context such as a gene locus) or in genetically modified form. An isolated nucleic acid molecule can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The nucleic acid molecule, preferably, is double or single stranded DNA including cDNA or RNA. The term encompasses single as well as double stranded nucleic acid molecules. Moreover, comprised are also chemically modified nucleic acid molecules including naturally occurring modified nucleic acid molecules such as glycosylated or methylated nucleic acid molecules or artificial modified ones such as biotinylated nucleic acid molecules.

In the studies underlying the present invention, advantageously, nucleic acid molecules where identified encoding novel dehydratasedehydrateses from *Brassica napus* and *Euglena gracilis*. In particular, the *Brassica napus* and *Euglena gracilis* dehydratasedehydratase BN-7, BN-G6 and EG-L3 dehydratases have been identified. Each of these dehydratasedehydratases are capable of removing a hydroxyl group from 3-hydroxy-acyl-CoA as part of the elongation process for fatty acids. For example, the expression of the BN-7, BN-G6 and EG-L3 dehydratases in a *Saccharomyces cerevisae* mutant not been able to elongate fatty acids has been found to restore the elongation process dehydratasedehydratasedehydratase Also preferably, the nucleic acid molecule of the present invention further comprises a nucleotide sequence encoding a heterologous polypeptide.

The present invention contemplates a vector comprising the nucleic acid molecule of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the nucleic acid molecules of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, 2$^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

More preferably, the vector of the present invention is an expression vector. In such an expression vector, the nucleic acid molecule is operatively linked to expression control sequences (also called "expression cassette") allowing expression in prokaryotic or eukaryotic cells or isolated fractions thereof. Expression of said polynucleotide comprises transcription of the nucleic acid molecule, preferably, into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the nucleic acid molecule or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-111113-B1, λgt11 or pBdCI, in *Streptomyces* pIJ101, pIJ364, pIJ702 or pIJ361, in *Bacillus* pUB110, pC194 or pBD214, in *Coryne-* bacterium pSA77 or pAJ667. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170:31-39).

The following promoters and expression control sequences may be, preferably, used in an expression vector according to the present invention. The cos, tac, trp, tet, trp-tet, lpp, lac, lpp-lac, lacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, MFa, AC, P-60, CYC1, GAPDH, TEF, rp28, ADH are, preferably, used or from plant the promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or the ubiquitin or phaseolin promoter. Also preferred in this context are inducible promoters, such as the promoters described in EP A 0 388 186 (benzylsulfonamide-inducible), Plant J. 2, 1992: 397-404 (Gatz et al., tetracyclin-inducible), EP A 0 335 528 (abscisic-acid-inducible) or WO 93/21334 (ethanol- or cyclohexenol-inducible). Further suitable plant promoters are the promoter of cytosolic FBPase or the ST-LSI promoter from potato (Stockhaus et al., EMBO J. 8, 1989, 2445), the phosphoribosyl-pyrophosphate amidotransferase promoter from *Glycine max* (Genbank accession No. U87999) or the node-specific promoter described in EP-A-0 249 676. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially advantageous promoters are seed-specific promoters which can be used for monocotyledonous or dicotyledonous plants and which are described in U.S. Pat. No. 5,608,152 (napin promoter from oilseed rape), WO 98/45461 (oleosin promoter from Arobidopsis, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for example for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890.

The nucleic acid molecule of the present invention can be expressed in single-cell plant cells (such as algae), see Falciatore et al., 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen et al., EMBO J. 3 (1984) 835 et seq.) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey et al., EMBO J. 8 (1989) 2195-2202) such as those which are derived from plant viruses such as 35S CAMV (Franck et al., Cell 21 (1980) 285-294), 19S CaMV (see also U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable promoters, for example the pathogen-induced PRP1-gene promoter (Ward et al., Plant Mol. Biol. 22 (1993) 361-366), the heat-inducible hsp80 promoter from tomato (U.S. Pat. No. 5,187, 267), the cold-inducible alpha-amylase promoter from potato (WO 96/12814) or the wound-inducible pinll promoter (EP A 0 375 091). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein et al., Mol. Gen. Genet., 1991, 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Suitable promoters to be taken into consideration are the Ipt2 or Ipt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the sorghum kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, J., Fritsch, E. F., and Maniatis, T., Molecular Cloning: A Laboratory Manual, 2$^{nd}$ edition, Cold Spring Harbor Laboratory, Cold Spring Harbor Laboratory Press, Cold Spring Harbor, N.Y., 1989.

It follows from the above that, preferably, said vector is an expression vector. More preferably, the said nucleic acid molecule of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP.

The present invention, furthermore, relates to a host cell comprising the nucleic acid molecule of the invention or which is transformed with the vector of the invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Oleg* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, *lesquerella*, tallow tree, sheanuts, tungnuts, kapok fruit, poppy seed, jojoba seeds and *perilla*.

Also preferably, said host cell is a microbial cell. More preferably, said microbial cell is selected from the group consisting of *Candida, Cryptococcus, Lipomyces, Rhodosporidium, Yarrowia, Thraustochytrium, Pythium, Schizochytrium* and *Crythecodinium*.

The present invention relates to a plant or plant seed comprising the nucleic acid molecule of the invention, the vector of the invention or the host cell of the invention.

Preferred plants to be used for introducing the nucleic acid molecule or the vector of the invention are plants which are capable of synthesizing fatty acids, such as all dicotyledonous or monocotyledonous plants, algae or mosses. It is to be understood that host cells derived from a plant may also e used for producing a plant according to the present invention. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum, Ditrichaceae* such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbine, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta [manihot]* or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chuff, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassaya, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as published, and cited, in: Plant Molecular Biology and Biotechnology (CRC Press, Boca Raton, Fla.), chapter 6/7, pp. 71-119 (1993); F.F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

The present invention also provides for a method of producing a polypeptide comprising culturing the host cell of the invention in an appropriate culture medium to, thereby, produce the polypeptide encoded by a nucleic acid molecule of the invention.

The polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. A polypeptide obtained by the said method includes variant polypeptides which are post-translationally modified, e.g., phosphorylated or myristylated, or which are processed on either RNA or protein level.

In principle, the present invention, however, relates to a polypeptide encoded by the nucleic acid molecule of the present invention.

The term "polypeptide" as used herein encompasses essentially purified polypeptides or polypeptide preparations comprising other proteins in addition. Moreover, the term also, preferably, includes polypeptides which are present in a host cell, plant or plant seed wherein the said host cell, plant or plant seed is not the biological source in which the polypeptide occurs naturally. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like. The terms "polypeptide", "peptide" or "protein" are used interchangeable throughout this specification. As referred to above, the polypeptide of the present invention shall exhibit dehydratase activity and, thus, can be used for the manufacture of unsaturated fatty acids, either in a host cell or in a transgenic animal or plant as described elsewhere in this specification.

The present invention also relates to an antibody which specifically recognizes the polypeptide of the present invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention shall specifically bind (i.e. does not cross react with other polypeptides or peptides) to the polypeptide of the invention. Specific binding can be tested by various well known techniques.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of compounds interacting with the proteins according to the invention.

Encompassed by the present invention is a method for producing an unsaturated fatty acid, comprising culturing the host cell of the invention or the plant or plant seed of the invention such that the unsaturated fatty acid is produced.

Also contemplated is a method of modulating the production of an unsaturated fatty acid comprising culturing the host cell of the invention or the plant or plant seed of the invention, such that modulation of the production of an unsaturated fatty acid occurs.

In a preferred embodiment of the methods of the present invention, said methods further comprises the step of recovering the unsaturated fatty acid from said culture.

The present invention, further, relates to a method of producing an unsaturated fatty acid comprising contacting a composition comprising at least one dehydratase target molecule with at least one polypeptide of the invention under conditions such that the unsaturated fatty acid is produced.

The term "unsaturated fatty acid" or "elongated fatty acid" as used herein, preferably, encompasses compounds having a structure as shown in the general formula I

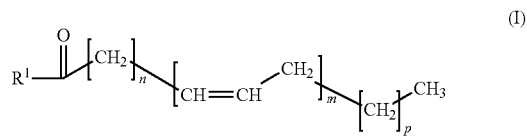

wherein the variables and substituents in formula I are
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

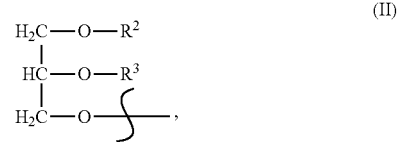

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl,
$R^3$=hydrogen, saturated or unsaturated $C_2$-$C_{24}$-alkylcarbonyl, or $R^2$ and $R^3$ independently of each other are a radical of the formula Ia:

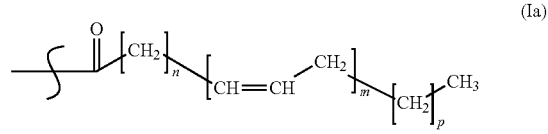

n=2, 3, 4, 5, 6, 7 or 9, m=2, 3, 4, 5 or 6 and p=0 or 3;
Preferably, $R^1$ in the general formula I is hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

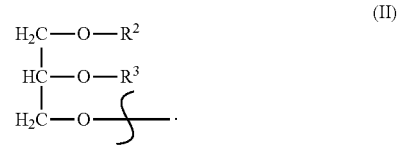

The abovementioned radicals of $R^1$ are always bonded to the compounds of the general formula I in the form of their thioesters.

Preferably, $R^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl. Moreover, alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{1-10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

Preferably, $R^3$ in the formula II is hydrogen, saturated or unsaturated $C_2$-$C_{24}$-alkylcarbonyl. Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl- or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds, are preferred. Preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Particularly preferred are saturated or unsaturated $C_{20}$-$C_{22}$-alkylcarbonyl radicals such as $C_{20}$-alkylcarbonyl or $C_{22}$-alkylcarbonyl radicals which comprise one or more double bonds. These preferred radicals can comprise two, three, four, five or six double bonds. The particularly preferred radicals with 20 or 22 carbon atoms in the fatty acid chain comprise up to six double bonds, advantageously two, three, four or five double bonds, especially preferably two, three or four double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The unsaturated fatty acids according to the present invention are, preferably, polyunsaturated fatty acids (PUFAs). The polyunsaturated fatty acids according to the invention advantageously comprise at least two, advantageously three, four, five or six, double bonds. The fatty acids especially advantageously comprise two, three, four or five double bonds. Unsaturated fatty acids, preferably, comprise 20 or 22 carbon atoms in the fatty acid chain. Saturated fatty acids are advantageously reacted to a minor degree, or not at all, by the nucleic acids used in the process. To a minor degree is to be understood as meaning that the saturated fatty acids are reacted with less than 5% of the activity, advantageously less than 3%, especially advantageously with less than 2% of the activity in comparison with polyunsaturated fatty acids. These fatty acids which have been produced can be produced in the process as a single product or be present in a fatty acid mixture.

Advantageously, the substituents $R^2$ or $R^3$ in the general formulae I and II independently of one another are saturated or unsaturated $C_{20}$-$C_{22}$-alkylcarbonyl; especially advantageously, are independently of one another unsaturated $C_{20}$- or $C_{22}$-alkylcarbonyl with at least two double bonds.

The polyunsaturated fatty acids according to the present invention are, preferably, bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms. In accordance with the method of the present invention, preferred are the long-chain fatty acids, especially the long chain PUFAs (LCPUFAs) of $C_{20}$- and/or $C_{22}$-fatty acids.

Preferred unsaturated fatty acids in the sense of the present invention are selected from the group consisting of DGLA 20:3 (8,11,14), AA 20:4 (5,8,11,14), EPA 20:5 (5,8,11,14,17), DPA 22:5 (4,7,10,13,16), and DHA 22:6 (4,7,10,13,16,19), 20:4 (8,11,14,17).

The term "dehydrates target molecule", preferably, encompasses substrates of the polypeptides of the invention. A particular preferred target molecule is 3-hydroxyacyl-ACP or 3-hydroxyacyl-CoA of GLA 18:3 (6,9,12), DGLA 20:3 (8,11,14), AA 20:4 (5,8,11,14), and eicosapentaenoic acid 20:5 (5,8,11,14,17).

The present invention also relates to a method of producing a host cell, plant or plant seed capable of generating an unsaturated fatty acid comprising introducing into said host cell, plant or plant seed the nucleic acid molecule of the present invention or the vector of the present invention.

The present invention provides for a method for the manufacture of an oil comprising the steps of the aforementioned methods and the further step of formulating an oil comprising the said unsaturated fatty acid.

The present invention includes an oil produced by the plant or plant seed of the invention or obtainable by the method of the invention.

The term "oil" refers to a fatty acid mixture comprising unsaturated or saturated, preferably esterified, fatty acid(s). The oil is preferably high in polyunsaturated free or, advantageously, esterified fatty acid(s), in particular the preferred LCPUFAs referred to herein above. The amount of unsaturated esterified fatty acids preferably amounts to approximately 30%, a content of 50% is more preferred, a content of 60%, 70%, 80% or more is even more preferred. For the analysis, the fatty acid content can, for example, be determined by GC after converting the fatty acids into the methyl esters by transesterification. The oil can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism. The oil, however, shall have a non-naturally occurring composition with respect to the unsaturated fatty acid. Moreover, the oil of the invention may comprise other molecular species as well. Specifically, it may comprise minor impurities of the nucleic acid molecules of the invention. Such impurities, however, can be detected only by highly sensitive techniques such as PCR.

The present invention also includes a method for the manufacture of a medicament comprising the steps of the methods of the invention and the further step of formulating medicament comprising the said unsaturated fatty acid.

The term "medicament" is used herein interchangeably with the term "pharmaceutical composition" explained in detail below. The term "medicament" or "pharmaceutical composition" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. However, depending on the subject and the mode of administration, the quantity of substance administration may vary over a wide range.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

For cosmetic applications, the compounds referred to herein as pharmaceutically active ingredients of the medicament can be formulated as a hair tonic, a hair restorer composition, a shampoo, a powder, a jelly, a hair rinse, an ointment, a hair lotion, a paste, a hair cream, a hair spray and/or a hair aerosol.

The present invention relatest to a medicament comprising the nucleic acid molecule, the vector, the host cell, the plant or plant seed or the oil of the present invention.

Moreover, the present invention relates to the use of the nucleic acid molecule, the vector, the host cell, the plant or plant seed or the oil of the invention for the manufacture of animal feed, a dietary supplement, or food.

Furthermore, the present invention relates to a cell comprising a nucleic acid molecule selected from the group consisting of:
  a) a nucleic acid molecule comprising the nucleotide sequence of SEQ ID
     NO: 1, 3, 5, 7 or 9, wherein the nucleic acid molecule is disrupted by at least one technique selected from the group consisting of a point mutation, a truncation, an inversion, a deletion, an addition, a substitution and homologous recombination;
  b) a nucleic acid molecule comprising the nucleotide sequence of SEQ ID NO: 1, 3, 5, 7 or 9, wherein the nucleic acid molecule comprises one or more nucleic acid modifications as compared to the sequence set forth in SEQ ID NO: 1, 3, 5, 7 or 9, wherein the modification is selected from the group consisting of a point mutation, a truncation, an inversion, a deletion, an addition and a substitution; and
  c) a nucleic acid molecule comprising the nucleotide sequence of SEQ ID NO: 1, 3, 5, 7 or 9, wherein the regulatory region of the nucleic acid molecule is modified relative to the wild-type regulatory region of the molecule by at least one technique selected from the group consisting of a point mutation, a truncation, an inversion, a deletion, an addition, a substitution and homologous recombination.

In the following, further preferred embodiments of the present invention are described in more detail.

The use of the nucleic acid molecules and polypeptides of the present invention provides a means for modulating, for example, enhancing, the production of desired elongated fatty acids. For example, the introduction of these dehydratasedehydratase nucleic acid and polypeptide molecules in microbial and plant cells, for example, under the control of a seed-specific promoter, will allow for the enhanced production of unsaturated fatty acids in oilseeds, such as AA 20:4 (5,8,11,14), EPA 20:5 (5,8,11,14,17), DPA 22:5 (4,7,10,13,16) and DHA 22:6 (4,7,10,13,16,19),.

Accordingly, in one aspect, the present invention is directed to an isolated nucleic acid molecule selected from the group consisting of a) an isolated nucleic acid molecule encoding dehydratasedehydratases from the genus *Brassica* or *Euglena*, or a complement thereof; b) an isolated nucleic acid molecules including the nucleotide sequence of SEQ ID NO:1, 3, 5, 7 or 9, or a complement thereof; c) an isolated nucleic acid molecule which encodes a polypeptide including the amino acid sequence of SEQ ID NO:2 or 4, or a complement thereof; d) an isolated nucleic acid molecule which encodes a naturally occurring allelic variant of a polypeptide including the amino acid sequence of SEQ ID NO:2 or 4, or a complement thereof; e) an isolated nucleic acid molecule including a nucleotide sequence which is at least 50% identical to the entire nucleotide sequence of SEQ ID NO:1 or 3, or a complement thereof; f) an isolated nucleic acid molecule including a nucleotide sequence which hybridizes to the complement of the nucleotide sequence of SEQ ID NO:1 or 3 under stringent conditions, or a complement thereof; g) an isolated nucleic acid molecule including a fragment of at least 15 contiguous nucleotides of the entire nucleotide sequence of SEQ ID NO:1 or 3, or a complement thereof. In a particular embodiment, the nucleic acid molecule encodes a dehydratasedehydratase protein having an activity of catalyzing the removal of an hydroxyl group from a enoyl-CoA molecule, for example the removal of the hydroxyl group from 3-hydroxy-eicosatrienoyl-CoA, 3-hydroxy-eicosatetraenoyl-CoA, 3-hydroxy-docosatetraenoyl-CoA and 3-hydroxyl-docosapentaenoyl-CoA of the fatty acid and h) an isolated nucleic acid molecule which hybridizes to the complement of the nucleotide sequence of SEQ ID NO:1, SEQ ID NO:3, SEQ ID NO:5, SEQ ID NO:7 and SEQ ID NO:9 in 6× sodium chloride/sodium citrate (SSC) at 65° C., or a complement thereof. In another embodiment, the isolated nucleic acid molecule further includes a nucleotide sequence encoding a heterologous polypeptide.

In another aspect, the invention is directed to a vector, for example, an expression vector, including a nucleic acid molecule of the invention. In a particular embodiment, the nucleic acid molecule may be under the control of a seed-specific promoter, for example, Conlinin 1, Conlinin 2, napin and LuFad3.

In another aspect, the invention is directed to a host cell transfected with the expression vector including a nucleic acid molecule of the invention. The host cell may be a plant cell, for example, a plant cell from an oilseed crop, including, but not limited to, flax (*Linum* sp.), rapeseed (*Brassica* sp.), soybean (Glycine and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*.

Alternatively, the host cell may be a microbial cell, including, but not limited to *Candida, Cryptococcus, Lipomyces, Rhodosporidium, Yarrowia, Thraustochytrium, Pythium, Schizochytrium* and *Crythecodinium*.

In another aspect, the invention provides a method of producing a polypeptide by culturing a host cell of the invention in an appropriate culture medium to, thereby, produce the polypeptide, for example, a fatty acid dehydratase.

In yet another aspect, the invention provides isolated polypeptides selected from the group consisting of a) an isolated fatty acid dehydratasedehydratase polypeptide from *Brassica* and *Euglena*; b) an isolated polypeptide including the amino acid sequence of SEQ ID NO:2, 4, 6, 8 or 10; c) an isolated polypeptide including a naturally occurring allelic variant of a polypeptide including the amino acid sequence of SEQ ID NO:2, 4, 6, 8 or 10; d) an isolated polypeptide including an amino acid sequence encoded by a nucleic acid molecule including the nucleotide sequence of SEQ ID NO:1, 3, 5, 7 or 9; e) an isolated polypeptide which is encoded by a nucleic acid molecule including the nucleotide sequence which is at least 50% identical to the entire nucleotide sequence of SEQ ID NO:1, 3, 5, 7 or 9; f) an isolated polypeptide including an amino acid sequence which is at least 50% identical to the entire amino acid sequence of SEQ ID NO:2, 4, 6, 8 or 10; and g) an isolated polypeptide including a fragment of a polypeptide including the amino acid sequence of SEQ ID NO:2, 4, 6, 8 or 10, wherein the polypeptide fragment maintains a biological activity of the complete polypeptide. In a particular embodiment, the polypeptide is involved in the production of an elongated fatty acid. In another embodiment, the polypeptide catalyzes the formation of enoyl-acyl-CoA molecules by removal of an hydroxyl group ($H_2O$ is formed) from 3-hydroxy-acyl-CoA. In another embodiment, the polypeptide also includes a heterologous amino acid sequence.

In another aspect, the invention provides a method for producing an elongated fatty acid by culturing a host cell of the invention such that the elongated fatty acid is produced. In another aspect, the invention provides a method for producing an elongated fatty acid by contacting a composition including at least dehydratase the dehydratase target molecule with at least one polypeptide of the invention under conditions such that the elongated fatty acid is produced. In yet another aspect, the invention provides a method of producing a cell capable of generating an elongated fatty acid by introducing into the cell nucleic acid molecules of the invention, wherein the nucleic acid molecules encode a dehydratasedehydratase having an activity of catalyzing the removal of an hydroxyl-group from 3-hydroxy-acyl-CoA. In yet another aspect, the present invention is directed to a method of modulating, for example, enhancing, the production of a long chain unsaturated fatty acid by culturing a cell transformed with the expression vector of the invention, such that modulation of the production of the long chain unsaturated fatty acid occurs. In a further aspect, the present invention is directed to a method for the large scale production of a long chain unsaturated fatty acid by culturing a cell transformed with the expression vector of the invention. In certain embodiments, the expression of the nucleic acid molecule results in the modulation of the production of long chain unsaturated fatty acids including, but not limited to AA 20:4 (5,8,11,14), EPA 20:5 (5,8,11,14,17), DPA 22:5 (4,7,10,13,16), DHA 22:6 (4,7,10,13,16,19).

In one embodiment, the fatty acid produced by the foregoing methods may be recovered from the culture. In another embodiment, the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacao*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*. In a particular embodiment, the cell is *Brassica juncea*. In yet another embodiment, the cell is a microbial cell, for example, *Candida, Cryptococcus, Lipomyces, Rhodosporidium, Yarrowia, Thraustochytrium, Pythium, Schizochytrium* and *Crythecodinium*.

In yet another aspect, the present invention is directed to a host cell having a) a nucleic acid molecule including the nucleotide sequence of SEQ ID NO:1, 3, 5, 7 or 9, wherein the nucleic acid molecule is disrupted by at least one technique selected from the group consisting of a point mutation, a truncation, an inversion, a deletion, an addition, a substitution and homologous recombination, for example, such that the fatty acid dehydratasedehydratase activity is disrupted; b) a nucleic acid molecule having the nucleotide sequence of SEQ ID NO:1, 3, 5, 7 or 9, wherein the nucleic acid molecule includes one or more nucleic acid modifications as compared to the sequence set forth in SEQ ID NO:1, 3, 5, 7 or 9, wherein the modification is selected from the group consisting of a point mutation, a truncation, an inversion, a deletion, an addition and a substitution, for example, such that the modified nucleic acid molecule encodes a polypeptide retaining fatty acid dehydratasedehydratase activity; or c) a nucleic acid molecule having the nucleotide sequence of SEQ ID NO:1, 3, 5, 7 or 9, wherein the regulatory region of the nucleic acid molecule is modified relative to the wild-type regulatory region of the molecule by at least one technique selected from the group consisting of a point mutation, a truncation, an inversion, a deletion, an addition, a substitution and homologous recombination, for example, so as to modify (e.g., enhance) fatty acid dehydratasedehydratase expression and/or activity.

In other aspects, the invention is directed to a plant including a vector as described herein, and oils or seeds produced by the plant. In another aspect, the invention is directed to a composition including the oil and/or seed, wherein the composition is for use as animal feed, a dietary supplement or food. In another aspect, the invention is directed to a pharmaceutical composition comprising the seed or oil. In yet another aspect, the invention is directed to an long chain unsaturated fatty acid obtained by a method described herein. In a further aspect, the invention is directed to compositions including the long chain unsaturated fatty acids produced by a method described herein, wherein the composition is for use as animal feed, a dietary supplement, or food. In yet another aspect, the invention is directed to a pharmaceutical composition including the long chain unsaturated fatty acids produced by a method described herein. In another aspect, the invention is directed to a composition comprising the dehydratase polypeptides of the invention or the transgenic cells of the invention, for example, for use as animal feed, a dietary supplement, food or a pharmaceutical composition.

In the following, particular preferred embodiments of the present invention are described.

The present invention is based, at least in part, on the discovery of fatty acid dehydratasedehydratase, referred to interchangeably herein as "dehydratasedehydratases" or "dehydratasedehydratase" nucleic acid and protein molecules (e.g., BN-7, BN-G8 from *Brassica napus* (*B. napus*) and/or EG-S6, EG-FF4 and EG-L3 from *Euglena graclis* (*E. gracilis*)) BN-7, BN-G6, EG-S6, EG-FF4 and EG-L3). These novel molecules are members of the fatty acid dehydratasedehdratase family and are expressed in a multitude of organisms producing elongated fatty acids such as *Brassica napus* and *Euglena gracilis*, and many other plant, algal and fungal organisms. The present invention is further based, at least in part, on the discovery that the *B. Napus* and *E. gracilis* fatty acid dehydratasedehdratases (e.g., BN-7, BN-G8, EG-S6, EG-FF4 and EG-L3BN-7, BN-G6, EG-S6, EG-FF4 and EG-L3) catalyze the removal of an hydroxyl-group from a 3-hydroxy-acyl-CoA fatty acid. dehydrataseBN-7, BN-G6, EG-S6, EG-FF4 and EG-L3 dehydratasedehydratasedehydratasedehydratase Generally, the controlling steps in the production of long chain unsaturated fatty acids, i.e., the long chain unsaturated fatty acid biosynthetic pathway, are catalyzed by membrane-associated fatty acid dehydrataseelongase complexes. BN-7, BN-G6, EG-S6, EG-FF4 and EG-L3 Plants and most other eukaryotic organisms have specialized elongase system for the extension of fatty acids beyond C18 atoms. These elongase reactions have several important features in common with the fatty acid synthase complex (FAS). However, the elongase complex is different from the FAS complex as the complex is localized in the cytosol and are membrane bound, ACP is not involved and the elongase 3-keto-acyl-CoA-synthase catalyzes the condensation of malonyl-CoA with an acyl primer. The elongase complex consists of four components with different catalytic functions, the keto-acyl-synthase (condensation reaction of malonyl-CoA to acyl-CoA, creation of a 2 C atom longer keto-acyl-CoA fatty acid), the keto-acyl-reductase (reduction of the 3-keto group to a 3-hydroxy-group), the dehydratase (dehydration results in a 3-enoyl-acyl-CoA fatty acid) and the enoly-CoA-reductase (reduction of the double bond at position 3, release from the complex).For the production of long chain PUFA including, but not limiting arachidonic acid (AA 20:4 (5,8,11,14)), eicosapentaenoic acid (EPA 20:5 (5,8,11, 14,17)), docosapentaenoic acid (DPA 22:5 (4,7,10,13,16)), docosahexaenoic acid (DHA 22:6 (4,7,10,13,16,19)), the elongation reaction is essential. Higher plant do not have the necessary enzyme set to produce long chain polyunsaturated fatty acids (4 or more double bonds, 20 or more C atoms). Therefore the catalytic activities have to be transferred into plants. One critical step in the process of elongation is the dehydration reaction. Three new amino acid sequences could be identified from plants and an PUFA producing algae, which catalyze the dehydration activity. By delivering this dehydratase in combination with dehydratases and elongases increased levels of PUFA are produced.

In view of the involvement of long chain polyunsaturated fatty acids in various cellular processes including, but not limited to, forming the cellular membranes of various tissues and organelles in mammals (for example, nerve, retina, brain and immune cells), promoting the growth and development of the brain in infants, maintaining normal brain function in adults, affecting photoreceptor function, affecting the signal transduction process, activating rhodopsin, and developing rods and cones, the dehydratasedehdratases of the present invention can be used in combination with dehydratases and elongases as described e.g. in WO2005/083093 in the treatment of certain disorders, for example, those disorders characterized by aberrantly regulated growth, proliferation, or differentiation. For example, the dehydratasedehydratases of the present invention in combination with dehydratases and elongases as described e.g. in WO2005/083093 can be used in the treatment of diseases such as hypertension, diabetes, hypercholesterolemia, arthritis, atherosclerosis, depression, thrombosis, cancers (e.g., carcinoma, sarcoma, or leukemia), tumor angiogenesis and metastasis, skeletal dysplasia, hepatic disorders, myelodysplastic syndromes, atopic eczema, premenstrual syndrome, and hematopoietic, inflammatory and/or myeloproliferative disorders. Other disorders which may be treated by the methods and compositions of the present invention include, those disorders related to angiogenesis including, but not limited to, hereditary hemorrhagic telangiectasia type 1, fibrodysplasia ossificans progressiva, idiopathic pulmonary fibrosis, and Klippel-Trenaunay-Weber syndrome.

As used herein, the term "fatty acid" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18) and which may be saturated or unsaturated. "Unsaturated" fatty acids contain cis double bonds between the carbon atoms. Unsaturated fatty acids encompassed by the present invention include, for example, DHA, EPA and ARA. "Polyunsaturated" fatty acids contain more than one double bond, often arranged in a methylene interrupted system ($-CH=CH-CH_2-CH=CH-$).

Fatty acids are described herein by a numbering system in which the number before the colon indicates the number of carbon atoms in the fatty acid. In the case of unsaturated fatty acids, the number after the colon is the number of double bonds that are present followed by a number in parentheses that indicates the position of the double bonds. Each number in parenthesis is the lower numbered carbon atom of the two connected by the double bond. For example, oleic acid can be described as 18:1(9) and linoleic acid can be described as 18:2(9,12) indicating 18 carbons, one double bond at carbon 9 and two double bonds at carbons 9 and 12, respectively. The term "family" when referring to the protein and nucleic acid molecules of the present invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics. "dehydratasedehydratase" is used interchangeably herein with a "dehydratasedehydratase activity," "biological activity of a dehydratasedehydratase," or "functional activity of a dehydratasedehydratase" and includes an activity exerted or mediated by a dehydratasedehydratase protein, polypeptide or nucleic acid molecule on a dehydratasedehydratase responsive cell or on a dehydratasedehydratase substrate, as determined in vivo or in vitro, according to standard techniques. In one embodiment, a dehydratase dehydrataseactivity is a direct activity such as an association with a dehydratase dehydratasetarget molecule. In another embodiment, a dehydratase dehydratasedirect activity also includes the removal of a 3-hydroxyl-group and the formation of an 3-enoyl-acyl-CoA fatty acid molecule.

As used herein, a "target molecule" or "binding partner" is a molecule, for example, a molecule involved in the synthesis of long chain polyunsaturated fatty acids, for example, an intermediate fatty acid (such as an unsaturated fatty acid on which the incorporation of a further double bond is desired) or a saturated fatty acid, with which a dehydratase protein binds or interacts in nature such that a dehydratase-mediated function is achieved. In particular embodiments, the target molecule or binding partner may be any of AA 20:4 (5,8,11,14), eicosadienoic acid 20:2 (11,14), docosapentaenoic acid 22:5 (7,10,13,16,19) and docosahexaenoic acid 22:6 (4,7,10,13, 16,19).

Various aspects of the invention are described in further detail in the following subsections:

I. Isolated Nucleic Acid Molecules

One aspect of the invention pertains to isolated nucleic acid molecules that encode dehydratase proteins or biologically active portions thereof. In another aspect, the invention is directed to nucleic acid fragments sufficient for use as hybridization probes to identify dehydratase-encoding nucleic acid molecules (e.g., dehydratase mRNA) and fragments for use as PCR primers for the amplification or mutation of dehydratase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated dehydratase nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3 5, 7, 9, or a portion thereof, can be isolated using standard molecular biology techniques and the sequence information provided herein. Using all or a portion of the nucleic acid sequence of SEQ ID NO:1, 3 5, 7, 9 as hybridization probes, dehydratase nucleic acid molecules can be isolated using standard hybridization and cloning techniques (e.g., as described in Sambrook, J. et al. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, 3 5, 7, 9, can be isolated by the polymerase chain reaction (PCR) using synthetic oligonucleotide primers designed based on the sequence of SEQ ID NO:1, 3 5, 7, 9.

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to dehydratase nucleotide sequences can be prepared by standard synthetic techniques, e.g., using an automated DNA synthesizer.

In still another embodiment, an isolated nucleic acid molecule of the invention comprises a nucleic acid molecule which is a complement of the nucleotide sequence shown in SEQ ID NO:1, 3 5, 7, 9, or a portion of any of these nucleotide sequences. A nucleic acid molecule which is complementary to the nucleotide sequence shown in SEQ ID NO:1, 3 5, 7, 9 is one which is sufficiently complementary to the nucleotide sequence shown in SEQ ID NO:1, 3 5, 7, 9, such that it can hybridize to the nucleotide sequence shown in SEQ ID NO:1, 3 5, 7, 9, thereby forming a stable duplex. In a particular embodiment, the complementary sequence of the invention are exact complements of the nucleic acid molecules of the invention, for example, a nucleotide sequence of SEQ ID NO:1, 3 5, 7, 93, a nucleotide sequence encoding a polypeptide of SEQ ID NO:2, 4, 6, 8, 10, an allelic variant thereof, and a nucleotide sequence of at least 70% identity to the nucleotide sequence of SEQ ID NO:1, 3 5, 7, 9. For example, the complement may be a full and complete complement of a nucleic acid molecule of the invention, for example, the nucleotide sequence of SEQ ID NO:1.

In still another embodiment, an isolated nucleic acid molecule of the present invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical to the nucleotide sequence shown in SEQ ID NO:1, 3 5, 7, 9 (e.g., to the entire length of the nucleotide sequence), or a portion or complement of any of these nucleotide sequences. Ranges and identity values intermediate to the above-recited ranges (e.g., 70-90% identical or 80-95% identical) are also intended to be encompassed by the present invention. For example, ranges of identity values using a combination of any of the above values recited as upper and/or lower limits are intended to be included.

Moreover, the nucleic acid molecule of the invention can comprise only a portion of the nucleic acid sequence of SEQ ID NO:1, 3 5, 7, 9, for example, a fragment which can be used as a probe or primer or a fragment encoding a portion of a dehydratase protein, e.g., a biologically active portion of a dehydratase protein. The nucleotide sequence determined from the cloning of the dehydratase gene allows for the generation of probes and primers designed for use in identifying and/or cloning other dehydratase family members, as well as dehydratase homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3 5, 7, 9, of an antisense sequence of SEQ ID NO:1, 3 5, 7, 9, or of a naturally occurring allelic variant or mutant of SEQ ID NO:1, 3 5, 7, 9.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the dehydratase nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment, a set of primers is provided, e.g., primers suitable for use in a PCR, which can be used to amplify a selected region of a dehydratase sequence, e.g., a domain, region, site or other sequence described herein. The primers should be at least 5, 10, 15, 20, 25, 30, 35, 40, 45 or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a dehydratase protein, such as by measuring a level of a dehydratase-encoding nucleic acid in a sample of cells from a subject, e.g., detecting dehydratase mRNA levels or determining whether a genomic dehydratase gene has been mutated or deleted.

A nucleic acid fragment encoding a "biologically active portion of a dehydratase protein" can be prepared by isolating a portion of the nucleotide sequence of SEQ ID NO:1, 3 5, 7, 9, which encodes a polypeptide having a dehydratase biological activity (the biological activities of the dehydratase proteins are described herein), expressing the encoded portion of the dehydratase protein (e.g., by recombinant expression in vitro) and assessing the activity of the encoded portion of the dehydratase protein. In an exemplary embodiment, the nucleic acid molecule is at least 50, 100, 150, 200, 250, 300, 350, 400, 450, 500, 550, 600, 650, 700, 750, 1000, 1250, 1300, 1350 or 1400 or more nucleotides in length and encodes a protein having a dehydratase activity (as described herein).

The invention further encompasses nucleic acid molecules that differ from the nucleotide sequence shown in SEQ ID NO:1, 3 5, 7, 9 due to degeneracy of the genetic code and thus encode the same dehydratase proteins as those encoded by the nucleotide sequence shown in SEQ ID NO:1, 3 5, 7, 9. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2, 4, 6, 8 or 10. In yet another embodiment, the nucleic acid molecule encodes the amino acid sequence of human dehydratase. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the dehydratase proteins. Such genetic polymorphism in the dehydratase genes may exist among individuals within a population due to natural allelic variation.

As used herein, the terms "gene" and "recombinant gene" refer to nucleic acid molecules which include an open reading frame encoding a dehydratase protein, e.g., oilseed dehydratase protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, 4, 6, 8 or 10. Moreover, the nucleic acid molecule may hybridize to a complement of a nucleic acid molecule comprising SEQ ID NO:1, 3 5, 7, 9, for example, under stringent hybridization conditions.

In addition to the B. Napus and E. gracilis fatty acid dehydratasedehydratase of SEQ ID NO:1, 3 5, 7, 9, it will be appreciated by those of ordinary skill in the art that DNA sequence polymorphisms that lead to changes in the amino acid sequences of dehydratase proteins may exist within a population (e.g., the B. Napus and E. gracilis population). Such genetic polymorphism in the fatty acid dehydratase gene may exist among individuals within a population due to natural variation. Such natural variations can typically result in 1-5% variance in the nucleotide sequence of the dehydratase gene. Allelic variants of the BN-7, BN-G6, EG-S6, EG-FF4 and EG-L3dehydrataseBN-7, BN-G6, EG-S6, EG-FF4 and EG-L3 dehydratase include both functional and non-functional dehydratasedehydratase proteins. Functional allelic variants are naturally occurring amino acid sequence variants of the dehydratasedehydratase protein that maintains the ability to, for example, (i) interact with a dehydratasedehydratase substrate or target molecule (for example, a fatty acid such as a an intermediate fatty acid); and/or (ii) remove a hydroxyl-group in dehydratasedehydratase substrate or target molecule. Functional allelic variants will typically contain only a conservative substitution of one or more amino acids of SEQ ID NO:2, 4, 6, 8 or 10, or a substitution, deletion or insertion of non-critical residues in non-critical regions of the protein.

Non-functional allelic variants are naturally occurring amino acid sequence variants of the dehydratase protein, e.g., BN-7, BN-G6, EG-S6, EG-FF4 and EG-L3 dehydrataseBN-7, BN-G6, EG-S6, EG-FF4 and EG-L3, that do not have the ability to, e.g., (i) interact with a dehydratasedehydratase substrate or target molecule (e.g., an intermediate fatty acid; and/or (ii) remove a hydroxyl-group in dehydratase dehydratasesubstrate or target molecule. Non-functional allelic variants will typically contain a non-conservative substitution, a deletion, or insertion, or premature truncation of the amino acid sequence of SEQ ID NO:2, 4, 6, 8 or 10, or a substitution, insertion, or deletion in critical residues or critical regions of the protein.

The present invention further provides orthologues (e.g., human orthologues of the dehydratase proteins). Orthologues of the B. napus and E. gracilis dehydratasedehydratase proteins are proteins that are isolated from other organisms and possess the same dehydratasedehydratase substrate or target molecule binding mechanisms, hydroxy-removal mechanisms, modulating mechanisms of growth and development of the brain in infants, maintenance mechanisms of normal brain function in adults, ability to affect photoreceptor function involved in the signal transduction process, ability to affect rhodopsin activation, development mechanisms of rods and/or cones, and/or modulating mechanisms of cellular growth and/or proliferation of the non-human dehydratase proteins. Orthologues of the dehydratase B. Napus and E. gracilis proteins can readily be identified as comprising an amino acid sequence that is substantially homologous to SEQ ID NO:2, 4, 6, 8 or 10.

Moreover, nucleic acid molecules encoding other dehydratasedehydratase family members and, thus, which have a nucleotide sequence which differs from the dehydratasedehydratase sequences of SEQ ID NO:2, 4, 6, 8 or 10 are intended to be within the scope of the invention. For example, another dehydratasedehydratase cDNA can be identified based on the nucleotide sequence of SEQ ID NO:2, 4, 6, 8 or 10BN-7, BN-G6, EG-S6, EG-FF4 or EG-L3. Moreover, nucleic acid molecules encoding dehydratase proteins from different species, and which, thus, have a nucleotide sequence which differs from the dehydratase sequences of SEQ ID NO:1, 3 5, 7, 9 are intended to be within the scope of the invention. dehydrataseBN-7, BN-G6, EG-S6, EG-FF4 or EG-L3

Nucleic acid molecules corresponding to natural allelic variants and homologues of the dehydratase cDNAs of the invention can be isolated based on their homology to the dehydratase nucleic acids disclosed herein using the cDNAs disclosed herein, or a portion thereof, as a hybridization probe according to standard hybridization techniques under stringent hybridization conditions.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 5, 7 or 9. In other embodiment, the nucleic acid is at least 50, 100, 150, 200, 250, 300, 350, 400, 450, 500, 550, 600, 650, 700, 750, 1000, 1250, 1300, 1350 or 1400 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_n$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}[Na^+]$)+0.41(% G+C)−(600/N), where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2×SSC, 1% SDS.

Preferably, an isolated nucleic acid molecule of the invention that hybridizes under stringent conditions to the sequence of SEQ ID NO:1, 3, 5, 7 or 9 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the dehydratase sequences that may exist in the population, the skilled artisan will further appreciate that changes can be introduced by mutation into the nucleotide sequences of SEQ ID NO:1, 3, 5, 7 or 9, thereby leading to changes in the amino acid sequence of the encoded dehydratase proteins, without altering the functional ability of the dehydratase proteins. For example, nucleotide substitutions leading to amino acid substitutions at "non-essential" amino acid residues can be made in the sequence of SEQ ID NO:1, 3, 5, 7 or 9. A "non-essential" amino acid residue is a residue that can be altered from the wild-type sequence of BN-7, BN-G6, EG-S6, EG-FF4 or EG-L3 e.g., the sequence of SEQ ID NO:2, 4, 6, 8 or 10 without altering the biological activity, whereas an "essential" amino acid residue is required for biological activity. For example, amino acid residues that are conserved among the dehydratase proteins of the present invention, e.g., those present in a heme-binding motif or a histidine motif, are predicted to be particularly unamenable to alteration. Furthermore, additional amino acid residues that are conserved between the dehydratase proteins of the present invention and other members of the fatty acid dehydratase family are not likely to be amenable to alteration.

Accordingly, another aspect of the invention pertains to nucleic acid molecules encoding dehydratase proteins that contain changes in amino acid residues that are not essential for activity. Such dehydratase proteins differ in amino acid sequence from SEQ ID NO:2, 4, 6, 8 or 10, yet retain biological activity. In one embodiment, the isolated nucleic acid molecule comprises a nucleotide sequence encoding a protein, wherein the protein comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical to SEQ ID NO:2, 4, 6, 8 or 10, e.g., to the entire length of SEQ ID NO:2 or 4.

An isolated nucleic acid molecule encoding a dehydratase protein homologous to the protein of SEQ ID NO:2, 4, 6, 8 or 10 can be created by introducing one or more nucleotide substitutions, additions or deletions into the nucleotide sequence of SEQ ID NO:1, 3,5, 7 or 9, such that one or more amino acid substitutions, additions or deletions are introduced into the encoded protein. Mutations can be introduced into SEQ ID NO:1, 3,5, 7 or 9 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a dehydratase protein is preferably replaced with another amino acid residue from the same side chain family. Alternatively, in another embodiment, mutations can be introduced randomly along all or part of a dehydratase coding sequence, such as by saturation mutagenesis, and the resultant mutants can be screened for dehydratase biological activity to identify mutants that retain activity. Following mutagenesis of SEQ ID NO:1, 3, 5, 7 or 9, the encoded protein can be expressed recombinantly and the activity of the protein can be determined.

In a preferred embodiment, a mutant dehydratase protein can be assayed for the ability to (i) interact with a dehydratase substrate or target molecule (e.g., an intermediate fatty acid); and/or (ii) form a double bond between carbon atoms in a dehydratase substrate or target molecule.

II. Isolated Dehydratase Proteins

One aspect of the invention pertains to isolated or recombinant dehydratase proteins and polypeptides, and biologically active portions thereof. In one embodiment, native dehydratase proteins can be isolated from cells or tissue sources by an appropriate purification scheme using standard protein purification techniques. In another embodiment, dehydratase proteins are produced by recombinant DNA techniques. Alternative to recombinant expression, a dehydratase protein or polypeptide can be synthesized chemically using standard peptide synthesis techniques.

An "isolated" or "purified" protein or biologically active portion thereof is substantially free of cellular material or other contaminating proteins from the cell or tissue source from which the dehydratase protein is derived, or substantially free from chemical precursors or other chemicals when chemically synthesized. The language "substantially free of cellular material" includes preparations of dehydratase protein in which the protein is separated from cellular components of the cells from which it is isolated or recombinantly produced. In one embodiment, the language "substantially free of cellular material" includes preparations of dehydratase protein having less than about 80%, 70%, 60%, 50%, 40%, or 30% (by dry weight) of non-dehydratase protein (also referred to herein as a "contaminating protein"), more preferably less than about 20% of non-dehydratase protein, still more preferably less than about 10% of non-dehydratase protein, and most preferably less than about 5% non-dehydratase protein. When the dehydratase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of dehydratase protein in which the protein is separated from chemical precursors or other chemicals which are involved in the synthesis of the protein. In one embodiment, the language "substantially free of chemical precursors or other chemicals" includes preparations of dehydratase protein having less than about 30% (by dry weight) of chemical precursors or non-dehydratase chemicals, more preferably less than about 20% chemical precursors or non-dehydratase chemicals, still more preferably less than about 10% chemical precursors or non-dehydratase chemicals, and most preferably less than about 5% chemical precursors or non-dehydratase chemicals. It should be understood that the proteins or this invention can also be in a form which is different than their corresponding naturally occurring proteins and/or which is still in association with at least some cellular components. For example, the protein can be associated with a cellular membrane.

As used herein, a "biologically active portion" of a dehydratase protein includes a fragment of a dehydratase protein which participates in an interaction between a dehydratase molecule and a non-dehydratase molecule (e.g., a dehydratase substrate such as fatty acid). Biologically active portions of a dehydratase protein include peptides comprising amino acid sequences sufficiently homologous to or derived from the dehydratase amino acid sequences, e.g., the amino acid sequences shown in SEQ ID NO:2, 4, 6, 8 or 10 which include sufficient amino acid residues to exhibit at least one activity of a dehydratase protein. Typically, biologically active portions comprise a domain or motif with at least one activity of the dehydratase protein, for example, the ability to (i) interact with a dehydratase substrate or target molecule (e.g., a fatty acid such as a saturated fatty acid and an intermediate fatty acid) and/or (ii) form a double bond between carbon atoms in a dehydratase substrate or target molecule. A biologically active portion of a dehydratase protein can be a polypeptide which is, for example, 10, 25, 50, 75, 100, 125, 150, 175, 200, 250, 300, 350, 400 or 450 or more amino acids in length.

In one embodiment, a biologically active portion of a dehydratase protein comprises a domain conserved among dehydratases and known to participate in a dehydratase activity. For example, at least one domain or motif conserved among the BN-7, BN-G6, EG-S6, EG-FF4 or EG-L3BN-7, BN-G6, EG-S6, EG-FF4 and EG-L3 amino acid sequences can be incorporated within the biologically active fragments in order to preserve dehydratase activity. Alternatively, at least one domain or motif conserved among the fatty acid dehydratases from different organisms, as depicted in FIG. 3, can be incorporated within the biologically active fragments in order to preserve dehydratase activity.

In a preferred embodiment, a dehydratase protein has an amino acid sequence shown in SEQ ID NO:2, 4, 6, 8 or 10. In other embodiments, the dehydratase protein is substantially identical to SEQ ID NO:2, 4, 6, 8 or 10 and retains the functional activity of the protein of SEQ ID NO:2, 4, 6, 8 or 10, yet differs in amino acid sequence due to natural allelic variation or mutagenesis, as described in detail in subsection I above. In another embodiment, the dehydratase protein is a protein which comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical to SEQ ID NO:2, 4, 6, 8 or 10.

In another embodiment, the invention features a dehydratase protein which is encoded by a nucleic acid molecule consisting of a nucleotide sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical to a nucleotide sequence of SEQ ID NO:1, 3, 5, 7 or 9, or a complement thereof. This invention further features a dehydratase protein which is encoded by a nucleic acid molecule consisting of a nucleotide sequence which hybridizes under stringent hybridization conditions to a complement of a nucleic acid molecule comprising the nucleotide sequence of SEQ ID NO:1, 3, 5, 7 or 9, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.,* 4:11-17 (1988)) which has been incorporated into the ALIGN program (version 2.0 or version 2.0 U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to dehydratase nucleic acid molecules of the invention. BLAST protein searches can be performed with the XBLAST program, score=50, wordlength=3 to obtain amino acid sequences homologous to dehydratase protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm.nih.gov.

III. Methods of Producing Unsaturated Fatty Acids

The present invention provides new and improved methods of producing long chain unsaturated fatty acids, e.g., long chain polyunsaturated fatty acids (LCPUFA's) and unsaturated fatty acids such as AA 20:4 (5,8,11,14), EPA 20:5 (5,8,11,14,17), DPA 22:5 (4,7,10,13,16), DHA 22:6 (4,7,10,13,16,19)

A. Recombinant Cells and Methods for Culturing Cells

The present invention further features recombinant vectors that include nucleic acid sequences that encode the gene products as described herein, preferably BN-7, BN-G6, EG-S6, EG-FF4 and EG-L3 gene products. The term recombinant vector includes a vector (e.g., plasmid) that has been altered, modified or engineered such that it contains greater, fewer or different nucleic acid sequences than those included in the native vector or plasmid. In one embodiment, a recombinant vector includes the nucleic acid sequence encoding at least one fatty acid dehydratase enzyme operably linked to regulatory sequences. The phrase "operably linked to regulatory sequence(s)" means that the nucleotide sequence of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant vector is introduced into a cell). Exemplary vectors are described in further detail herein as well as in, for example, Frascotti et al., U.S. Pat. No. 5,721,137, the contents of which are incorporated herein by reference.

The term "regulatory sequence" includes nucleic acid sequences which affect (e.g., modulate or regulate) expression of other (non-regulatory) nucleic acid sequences. In one embodiment, a regulatory sequence is included in a recombinant vector in a similar or identical position and/or orientation relative to a particular gene of interest as is observed for the regulatory sequence and gene of interest as it appears in nature, e.g., in a native position and/or orientation. For example, a gene of interest (e.g., a BN-7, BN-G6, EG-S6, EG-FF4 or EG-L3BN-7, BN-G6, EG-S6, EG-FF4 or EG-L3 gene) can be included in a recombinant vector operably linked to a regulatory sequence which accompanies or is adjacent to the gene in the natural organism (e.g., operably linked to "native" BN-7, BN-G6, EG-S6, EG-FF4 or EG-L3BN-7, BN-G6, EG-S6, EG-FF4 or EG-L3 regulatory sequence (e.g., to the "native" BN-7, BN-G6, EG-S6, EG-FF4 or EG-L3BN-7, BN-G6, EG-S6, EG-FF4 or EG-L3 promoter). Alternatively, a gene of interest (e.g., a BN-7, BN-G6, EG-S6, EG-FF4 or EG-L3BN-7, BN-G6, EG-S6, EG-FF4 or EG-L3 gene) can be included in a recombinant vector operably linked to a regulatory sequence which accompanies or is adjacent to another (e.g., a different) gene in the natural organism. For example, a BN-7, BN-G6, EG-S6, EG-FF4 or EG-L3BN-7, BN-G6, EG-S6, EG-FF4 or EG-L3 gene can be included in a vector operably linked to non-BN-7, BN-G6, EG-S6, EG-FF4 or EG-L3BN-7, BN-G6, EG-S6, EG-FF4 or EG-L3 regulatory sequences. Alternatively, a gene of interest (e.g., a BN-7, BN-G6, EG-S6, EG-FF4 or EG-L3BN-7, BN-G6, EG-S6, EG-FF4 or EG-L3 gene) can be included in a vector operably linked to a regulatory sequence from another organism. For example, regulatory sequences from other microbes (e.g., other bacterial regulatory sequences, bacteriophage regulatory sequences and the like) can be operably linked to a particular gene of interest.

Preferred regulatory sequences include promoters, enhancers, termination signals and other expression control elements (e.g., binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a cell (e.g., constitutive promoters and strong constitutive promoters), those which direct inducible expression of a nucleotide sequence in a cell (e.g., inducible promoters, for example, xylose inducible promoters) and those which attenuate or repress expression of a nucleotide sequence in a cell (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant vector of the present invention includes nucleic acid sequences that encode at least one gene product (e.g., BN-7, BN-G6, EG-S6, EG-FF4 or EG-L3BN-7, BN-G6, EG-S6, EG-FF4 or EG-L3) operably linked to a promoter or promoter sequence.

In a particular embodiment, seed-specific promoters are utilized to enhance the production of the desired unsaturated fatty acid. For example, U.S. Patent Publication No. 2003-0159174, published Aug. 21, 2003, the entire contents of which are hereby expressly incorporated by reference herein, describes the use of particular seed-specific promoters including, for example, Conlinin, Conlinin 2 and LuFad3 from the genus *Linum*. One skilled in the art will appreciate that other promoters, for example, seed-specific promoters such as napin, may be utilized to modulate, for example, enhance, the expression of the dehydratase nucleotide sequence.

In yet another embodiment, a recombinant vector of the present invention includes a terminator sequence or terminator sequences (e.g., transcription terminator sequences). The term "terminator sequences" includes regulatory sequences which serve to terminate transcription of mRNA. Terminator sequences (or tandem transcription terminators) can further serve to stabilize mRNA (e.g., by adding structure to mRNA), for example, against nucleases.

In yet another embodiment, a recombinant vector of the present invention includes antibiotic resistance sequences. The term "antibiotic resistance sequences" includes sequences which promote or confer resistance to antibiotics on the host organism. In one embodiment, the antibiotic resistance sequences are selected from the group consisting of cat (chloramphenicol resistance), tet (tetracycline resistance) sequences, erm (erythromycin resistance) sequences, neo (neomycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

The term "manipulated cell" includes a cell that has been engineered (e.g., genetically engineered) or modified such that the cell has at least one fatty acid dehydratase, e.g., BN-7, BN-G6, EG-S6, EG-FF4 or EG-L3BN-7, BN-G6, EG-S6, EG-FF4 or EG-L3, such that an unsaturated fatty acid is produced. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, for example, as compared to a corresponding wild-type or naturally occurring enzyme.

The term "overexpressed" or "overexpression" includes expression of a gene product (e.g., a fatty acid dehydratase) at a level greater than that expressed prior to manipulation of the cell or in a comparable cell which has not been manipulated. In one embodiment, the cell can be genetically manipulated (e.g., genetically engineered) to overexpress a level of gene product greater than that expressed prior to manipulation of the cell or in a comparable cell which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including, but not limited to, use of antisense nucleic acid molecules, for example, to block expression of repressor proteins).

In another embodiment, the cell can be physically or environmentally manipulated to overexpress a level of gene product greater than that expressed prior to manipulation of the cell or in a comparable cell which has not been manipulated. For example, a cell can be treated with or cultured in the presence of an agent known or suspected to increase transcription of a particular gene and/or translation of a particular gene product such that transcription and/or translation are enhanced or increased. Alternatively, a cell can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell that encodes an enzyme in a biosynthetic pathway, such that the level or activity of the biosynthetic enzyme in the cell is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a cell arises from the particular phenomenon of cells in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to, removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including, but not limited to, use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" cell of the present invention has been genetically engineered to overexpress a plant-derived gene or gene product or an microorganismally-derived gene or gene product. The term "plant-derived," "microorganismally-derived," or "derived-from," for example, includes a gene which is naturally found in a microorganism or a plant, e.g., an oilseed plant, or a gene product (e.g., BN-7, BN-G6, EG-S6, EG-FF4 or EG-L3) or which is encoded by a plant gene or a gene from a microorganism (e.g., encoded SEQ ID NO:1, SEQ ID NO:3, SEQ ID NO:5, SEQ ID NO:7 or SEQ ID NO:9).

The methodologies of the present invention feature recombinant cells which overexpress at least one fatty acid dehydratase. In one embodiment, a recombinant cell of the present invention has been genetically engineered to overexpress a *Claviceps purpurea* fatty acid dehydratase (e.g., has been engineered to overexpress at least one fatty acid dehydratase having the amino acid sequence of SEQ ID NO:2, 4, 6, 8 or 10 or encoded by the nucleic acid sequence of SEQ ID NO:1, 3, 5, 7 or 9). In another embodiment, the invention features a cell (e.g., a microbial cell) that has been transformed with a vector comprising a fatty acid dehydratase nucleic acid sequence (e.g., a fatty acid dehydratase nucleic acid sequence as set forth in SEQ ID NO:1, 3, 5, 7 or 9).

Another aspect of the present invention features a method of modulating the production of fatty acids comprising culturing cells transformed by the nucleic acid molecules of the present invention (e.g., a dehydratase) such that modulation of fatty acid production occurs (e.g., production of unsaturated fatty acids is enhanced). The method of culturing cells transformed by the nucleic acid molecules of the present invention (e.g., BN-7, BN-G6, EG-S6, EG-FF4 or EG-L3) to modulate the production of fatty acids is referred to herein as "biotransformation." The biotransformation processes can utilize recombinant cells and/or dehydratases described herein. The term "biotransformation process," also referred to herein as "bioconversion processes," includes biological processes which result in the production (e.g., transformation or conversion) of any compound (e.g., substrate, intermediate, or product) which is upstream of a fatty acid dehydratase or a compound (e.g., substrate, intermediate, or product) which is downstream of a fatty acid dehydratase, in particular, an unsaturated fatty acid. In one embodiment, the invention features a biotransformation process for the production of an unsaturated fatty acid comprising contacting a cell which overexpresses at least one fatty acid dehydratase with at least one appropriate substrate under conditions such that an unsaturated fatty acid is produced and, optionally, recovering the fatty acid. In a preferred embodiment, the invention features a biotransformation process for the production of unsaturated fatty acids comprising contacting a cell which overexpresses BN-7, BN-G6, EG-S6, EG-FF4 or EG-L3 with an appropriate substrate (e.g., an intermediate fatty acid) under conditions such that an unsaturated fatty acid (e.g., DHA, ARA or EPA) is produced and, optionally, recovering the unsaturated fatty acid. Conditions under which an unsaturated fatty acid is produced can include any conditions which result in the desired production of an unsaturated fatty acid.

The cell(s) and/or enzymes used in the biotransformation reactions are in a form allowing them to perform their intended function (e.g., producing a desired fatty acids). The cells can be whole cells, or can be only those portions of the cells necessary to obtain the desired end result. The cells can be suspended (e.g., in an appropriate solution such as buffered solutions or media), rinsed (e.g., rinsed free of media from culturing the cell), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall). The type of cell can be any cell capable of being used within the methods of the invention, e.g., plant, animal, or microbial cells.

The type of cell can be any cell capable of being used within the methods of the invention, e.g., plant, animal, or microbial cells, preferably a plant or microbial cell. In one embodiment, the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*. In another embodiment, the cell is *Brassica juncea*. U.S. Patent Publication No. 2003-0159174, published Aug. 21, 2003, the entire contents of which are hereby expressly incorporated by reference herein, provides extensive teaching on the transformation of plant cells to optimize production of a desired end product.

In yet another embodiment, the cell is a microbial cell, for example, *Candida*, *Cryptococcus*, *Lipomyces*, *Rhodosporidium*, *Yarrowia*, *Thraustochytrium*, *Pythium irregulare*, *Schizochytrium* and *Crythecodinium*. One skilled in the art will appreciate that other microbial cells can be used in accordance with the methods provided herein, for example, for the production of a desaturated fatty acid.

An important aspect of the present invention involves growing the recombinant plant or culturing the recombinant microorganisms described herein, such that a desired compound (e.g., a desired unsaturated fatty acid) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism (e.g., carbon sources or carbon substrate, for example complex carbohydrates such as bean or grain meal, starches, sugars, sugar alcohols, hydrocarbons, oils, fats, fatty acids, organic acids and alcohols; nitrogen sources, for example, vegetable proteins, peptones, peptides and amino acids derived from grains, beans and tubers, proteins, peptides and amino acids derived form animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., an unsaturated fatty acid). In one embodiment, microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., an unsaturated fatty acid). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents). Moreover, plants or microorganisms of the present invention can be cultured under controlled temperatures. The term "controlled temperature" includes any temperature which results in production of the desired product (e.g., an unsaturated fatty acid). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., an unsaturated fatty acid). A variety of such processes have been developed and are well-known in the art.

The phrase "culturing under conditions such that a desired compound (e.g., an unsaturated fatty acid, for example, DHA) is produced" includes maintaining and/or growing plants or microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a unsaturated fatty acid (e.g., DHA). Preferably, culturing is continued for a time sufficient to substantially reach maximal production of the unsaturated fatty acid. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of unsaturated fatty acids, for example, cells are cultured such that at least about 15 to 20 g/L of unsaturated fatty acids are produced, at least about 20 to 25 g/L unsaturated fatty acids are produced, at least about 25 to 30 g/L unsaturated fatty acids are produced, at least about 30 to 35 g/L unsaturated fatty acids are produced, at least about 35 to 40 g/L unsaturated fatty acids are produced (e.g., at least about 37 g/L unsaturated fatty acids) or at least about 40 to 50 g/L unsaturated fatty acids are produced. In yet another embodiment, microorganisms are cultured under conditions such that a preferred yield of unsaturated fatty acids, for example, a yield within a range set forth above, is produced in about 24 hours, in about 36 hours, in about 48 hours, in about 72 hours, or in about 96 hours.

In producing unsaturated fatty acids, it may further be desirable to culture cells of the present invention in the presence of supplemental fatty acid biosynthetic substrates. The term "supplemental fatty acid biosynthetic substrate" includes an agent or compound which, when brought into contact with a cell or included in the culture medium of a cell, serves to enhance or increase unsaturated fatty acid biosynthesis. Supplemental fatty acid biosynthetic substrates of the present invention can be added in the form of a concentrated solution or suspension (e.g., in a suitable solvent such as water or buffer) or in the form of a solid (e.g., in the form of a powder). Moreover, supplemental fatty acid biosynthetic substrates of the present invention can be added as a single aliquot, continuously or intermittently over a given period of time.

The methodology of the present invention can further include a step of recovering a desired compound (e.g., an unsaturated fatty acid). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the unsaturated fatty acid of interest (e.g., DHA).

Preferably, a desired compound of the present invention is "extracted," "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound is an unsaturated fatty acid that has been derivatized to a salt, the compound is preferably further free (e.g., substantially free) of chemical contaminants associated with the formation of the salt. When the desired compound is an unsaturated fatty acid that has been derivatized to an alcohol, the compound is preferably further free (e.g., substantially free) of chemical contaminants associated with the formation of the alcohol.

In an alternative embodiment, the desired unsaturated fatty acid is not purified from the plant or microorganism, for example, when the plant or microorganism is biologically non-hazardous (e.g., safe). For example, the entire plant or culture (or culture supernatant) can be used as a source of product (e.g., crude product). In one embodiment, the plant or culture (or culture supernatant) supernatant is used without modification. In another embodiment, the plant or culture (or culture supernatant) is concentrated. In yet another embodiment, the plant or culture (or culture supernatant) is pulverized, dried, or lyophilized.

B. High Yield Production Methodologies

A particularly preferred embodiment of the present invention is a high yield production method for producing unsaturated fatty acids, e.g., DHA, comprising culturing a manipulated plant or microorganism under conditions such that the unsaturated fatty acid is produced at a significantly high yield. The phrase "high yield production method," for example, a high yield production method for producing a desired compound (e.g., for producing an unsaturated fatty acid) includes a method that results in production of the desired compound at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing unsaturated fatty acids that includes culturing a manipulated plant or microorganism under conditions such that an unsaturated fatty acid is produced at a level greater than 2 g/L. In another embodiment, the invention features a high yield production method of producing unsaturated fatty acids that includes culturing a manipulated plant or microorganism under conditions such that an unsaturated fatty acid is produced at a level greater than 10 g/L. In another embodiment, the invention features a high yield production method of producing unsaturated fatty acids that includes culturing a manipulated plant or microorganism under conditions such that an unsaturated fatty acid is produced at a level greater than 20 g/L. In yet another embodiment, the invention features a high yield production method of producing unsaturated fatty acids that includes culturing a manipulated plant or microorganism under conditions such that an unsaturated fatty acid is produced at a level greater than 30 g/L. In yet another embodiment, the invention features a high yield production method of producing unsaturated fatty acids that includes culturing a manipulated plant or microorganism under conditions such that an unsaturated fatty acid is produced at a level greater than 40 g/L.

The invention further features a high yield production method for producing a desired compound (e.g., for producing an unsaturated fatty acid) that involves culturing a manipulated plant or microorganism under conditions such that a sufficiently elevated level of compound is produced within a commercially desirable period of time. In an exemplary embodiment, the invention features a high yield production method of producing unsaturated fatty acids that includes culturing a manipulated plant or microorganism under conditions such that an unsaturated fatty acid is produced at a level greater than 15-20 g/L in 36 hours. In another embodiment, the invention features a high yield production method of producing unsaturated fatty acids that includes culturing a manipulated plant or microorganism under conditions such that an unsaturated fatty acid is produced at a level greater than 25-30 g/L in 48 hours. In another embodiment, the invention features a high yield production method of producing unsaturated fatty acids that includes culturing a manipulated plant or microorganism under conditions such that an unsaturated fatty acid is produced at a level greater than 35-40 g/L in 72 hours, for example, greater that 37 g/L in 72 hours. In another embodiment, the invention features a high yield production method of producing unsaturated fatty acids that includes culturing a manipulated plant or microorganism under conditions such that an unsaturated fatty acid is produced at a level greater than 30-40 g/L in 60 hours, for example, greater that 30, 35 or 40 g/L in 60 hours. Values and ranges included and/or intermediate within the ranges set forth herein are also intended to be within the scope of the present invention. For example, unsaturated fatty acid production at levels of at least 31, 32, 33, 34, 35, 36, 37, 38 and 39 g/L in 60 hours are intended to be included within the range of 30-40 g/L in 60 hours. In another example, ranges of 30-35 g/L or 35-40 g/L are intended to be included within the range of 30-40 g/L in 60 hours. Moreover, the skilled artisan will appreciate that culturing a manipulated microorganism to achieve a production level of, for example, "30-40 g/L in 60 hours" includes culturing the microorganism for additional time periods (e.g., time periods longer than 60 hours), optionally resulting in even higher yields of an unsaturated fatty acid being produced.

IV. Compositions

The dehydratase nucleic acid molecules, proteins, and fragments thereof, of the invention can be used to produce long chain unsaturated fatty acids which can be incorporated into compositions. Compositions of the present invention include, e.g., compositions for use as animal feed, compositions for use as neutraceuticals (e.g., dietary supplements), and pharmaceutical compositions suitable for administration. Such pharmaceutical compositions typically comprise an unsaturated fatty acid and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a LCPUFA, or a fragment thereof, produced by the nucleic acid and protein molecules of the present invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with a LCPUFA in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The pharmaceutical compositions can be included in a container, pack, or dispenser together with instructions for administration.

FIGURES

FIG. 1 shows the nucleotide and amino acid sequences of dehydratases from Brassica napus (BN-7 and BNG8) as follows: (A) the cDNA sequence of the mRNA (SEQ ID NO:1, and 3) (FIG. 1A); the translated amino acid sequences (SEQ ID NO:2 and 4) (FIG. 1B).

FIG. 2 shows the nucleotide and amino acid sequence of a dehydratase from Euglena gracilis (EG-S6, EG-FF4 and EG-L3) as follows: the cDNA sequence of the mRNA (SEQ ID NO:5, 7 and 9) (FIG. 2A); the translated amino acid sequence (SEQ ID NO:6, 8 and 10) (FIG. 2B).

FIG. 3 shows an alignment of the amino acid of dehydratase from Brassica napus, Euglena gracilis (BN-7, BN-G8, EG-S6, EG-FF4 and EG-L3) and that of the dehydratase from Saccharomyces cerevisae YJL097W.

FIG. 4 is a complementation study with the dehydratases BN-7, BN-G8, EG-S6, EG-FF4 and EG-L3 cloned into the yeast expression vector YES2.1/V5His-TOPO and transformed into yeast strain YSC4034-97041153. The growing of yeast for BN-7, BN-G6 and EG-L3 shows for these sequences their dehydratase activity. EG-S6 and EG-FF4 do not exhibit dehydratase activity.

This invention is further illustrated by the following examples which should not be construed as limiting. The contents of all references, patents and published patent applications cited throughout this application, as well as the figures, are incorporated herein by reference.

EXAMPLES

Example 1

Organisms and Culture Conditions

For complementation studies, clones were transformed into the heterozygous magic marker strain YSC4034-97041153 from Open Biosystems, and positive clones were selected on DOB-uracil plates. For regeneration of haploids, the method outlined in Pan et al 2004 (Molecular Cell 16:487-496) was used. Briefly, cultures were grown overnight in DOB-uracil, then approximately 25 $OD_{600}$ of each culture was washed and resuspended in fresh media and grown for 3 hours. Cells were then suspended in sporulation media (1% potassium acetate, 0.005% zinc acetate), sporulated for 5 days and spread on haploid selection magic media plates (2% galactose, amino acid mix-uracil-leucine-histidine-arginine, 0.17% nitrogen base without amino acids or ammonium sulfate, 0.1% sodium glutamate) containing 200 mg/L G418 and 60 mg/L canavanine.

Example 2

Cloning of BN-7, BN-G6, EG-S6, EG-FF4 and EG-L3 dehydratase cDNA

A Brassica napus EST, GB accession number CX192963, with a deduced translation product having similarity to that of the yeast gene YJL097W, was identified by database searches. Primers BNDH-F (5'-gttagtacatggcggggtctttctc-3') and BNDH-R (5'-tttttattccctcttggatttggag-3') were designed based on this sequence. *Brassica napus* RNA from immature seed was reverse-transcribed and the cDNA was used as a template for PCR with the proof-reading polymerase PfuUltra and primers BN-F and BN-R. PCR products were cloned into the vector pYES2.1/V5-His-TOPO. Clones containing inserts in the correct orientation were selected by PCR analysis and sequenced. Two clones with slightly different sequences, BN-G6 and BN-7, were obtained.

A *Euglena gracilis* EST, GB accession number EC672518, with a deduced translation product having similarity to that of the yeast gene YJL097W, was identified by database searches. The forward primer EDHR1 (5'-cggcgctgtgccagcatgtatg-3', SEQ ID NO:13) was used with the Marathon (BD Biosciences) AP1 primer to amplify the 5' end of the gene from *Euglena gracilis* cDNA constructed using the Marathon cDNA Amplification Kit. The deduced amino acid sequence of the 5' RACE product indicated the *Euglena gracilis* dehydratase appeared to have a very long N-terminal extension compared to the corresponding *Brassica napus* or yeast genes. Based on the sequence of the 5' RACE product, as well as those of Genbank sequences with homology to this 5' end, three primers, EGDH-LF (5'-ggaacatgcaccactttcggccg-3') EGDH-SF (5'-ggaacatgtacaacgctggccaagc-3') and EGDH-FF (5'-ggaacatggcggttttcaccaactacgtcc-3') were designed to amplify sequences starting at the most 5' methionine, the first methionine within the area of the deduced translation product having homology to the yeast and *Brassica* sequences, and the most N-terminal region of the Euglena gene with homology to the other genes, respectively. The last primer, EGDH-FF, included an engineered methionine start codon. RNA from *Euglena gracilis* was reverse-transcribed and the cDNA was used as a PCR template in reactions including one of the three forward primers along with EGDH-R (5'-CCAAGCTTGTGTCATTGATTCTTCTTCTCGG-3'). PCR products were cloned into the vector pYES2.1/V5-His-TOPO. Clones containing inserts in the correct orientation were selected by PCR analysis and sequenced. Three clones with inserts of differing lengths, EG-L3, EG-S6 and EG-FF4, were obtained.

A list of identified full-length coding sequences and the respective used primer sequences for obtaining them is shown in Table 1.

TABLE 1

List of full-length coding sequences and used primer sequences.

| Gene | Organism | SEQ ID NO: | Primer | SEQ ID NO: |
|---|---|---|---|---|
| BN-G6 | B. napus | 1 | BNDH-F 5'-gttagtacatggcggggtctttctc-3' BNDH-R 5'-tttttattccctcttggatttggag-3' | 11 12 |
| BN-7 | B. napus | 3 | BNDH-F 5'-gttagtacatggcggggtctttctc-3' BNDH-R 5'-tttttattccctcttggatttggag-3' | 11 12 |
| EG-L3 | E. gracilis | 9 | EGDH-LF 5'-ggaacatgcaccactttcggccg-3' EGDH-R 5'-CCAAGCTTGTGTCATTGATTCTTCTTCTCGG-3' | 14 17 |
| EG-FF4 | E. gracilis | 7 | EGDH-FF 5'-ggaacatggcggttttcaccaactacgtcc-3' EGDH-R 5'-CCAAGCTTGTGTCATTGATTCTTCTTCTCGG-3' | 15 17 |
| EG-S6 | E. gracilis | 5 | EGDH-SF 5'-ggaacatgtacaacgctggccaagc-3' EGDH-R 5'-CCAAGCTTGTGTCATTGATTCTTCTTCTCGG-3' | 16 17 |

A list of deduced amino acids from sequences described in Table 1 is shown in Table 2.

| Gene | Organism | SEQ ID NO: |
|---|---|---|
| BN-G6 | B. napus | 4 |
| BN-7 | B. napus | 2 |
| EG-L3 | E. gracilis | 10 |
| EG-FF4 | E. gracilis | 8 |
| EG-S6 | E. gracilis | 6 |

Example 3

Yeast Transformation and Growth Conditions

*S. cerevisiae* strain YSC4034-97041153 from Open Biosystems was transformed with the constructs (pYES2.11V5-His-TOPO-BN-G6, pYES2.11V5-His-TOPO-BN-7, pYES2.1/V5-His-TOPO-EG-L3, pYES2.1/V5-His-TOPO-EG-FF4, pYES2.1/V5-His-TOPO-EG-S6) using the S.C. EasyComp Transformation Kit (Invitrogen, Carlsbad, Calif.) with selection on uracil-deficient medium. For assessing the dehydratase activity complementation studies were done. For that purpose the heterozygous magic marker strain YSC4034-97041153 from Open Biosystems was used. This strain does not exhibit any dehydratase activity. As the dehydratase activity delivers elongated fatty acids and these fatty acids are required for cell growth and division, the respective yeast strain will not grow on medium not containing said elongated fatty acids.

Transformands were treated as described in Example 1 for growing conditions. After 3 days, colonies formed on plates spread with cells sporulated from cultures containing the plasmids EG-L3, BN-G6 and BN-7 while no colonies formed on plates spread with cells derived from cultures carrying the EG-S6, EG-FF4 or pYES2.1 clones (FIG. 4). Therefore both *Brassica napus* sequences and the long version of the *Euglena gracilis* sequence appear to be capable of complementing the lethal null mutation in the yeast 3-hydroxy acyl-CoA dehydratase gene YJL097W.

In summary, by complementation of a defective yeast mutant it could been shown that the dehydratase sequence EG-L3, BN-G6 and BN-7 are functional dehydratases.

Example 4

Expression of EG-L3, BN-G6 and BN-7 in Plants

To examine the utility of EG-L3, BN-G6 and BN-7 in the production of polyunsaturated fatty acids in plants, for example, for nutraceutical use, the EG-L3, BN-G6 and BN-7 gene was expressed in *Arabidopsis thaliana* under the control of a seed-specific *Brassica napus* napin storage protein promoter. The binary vector for plant expression containing the candidate gene was introduced by the in-planta *Agrobacterium*-infiltration approach into *A. thaliana* Col0. Transgenic mature seeds were analyzed for the production of unusual fatty acids by gas chromatography. Transgenic plants show increased levels of polyunsaturated fatty acids.

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella alpina* by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbiol. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant. Microbe Interact. 15, 303-312.

Okuley, J., Lightner, J., Feldmann, K., Yadav, N., Lark, E., and Browse, J. (1994). *Arabidopsis* FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Tudzynski, P., Correia, T., and Keller, U. (2001). Biotechnology and genetics of ergot alkaloids. Appl. Microbiol. Biotechnol. 57, 593-605.

All references cited in this specification are herewith incorporated by reference with respect to their entire disclosure content and the disclosure content specifically mentioned in this specification.

The invention claimed is:

1. An isolated nucleic acid molecule comprising at least one regulatory sequence operably linked to an heterologous nucleic acid sequence selected from the group consisting of:
   a) the nucleic acid sequence of SEQ ID NO: 1, 3, 7 or 9;
   b) a nucleic acid sequence encoding a polypeptide comprising the amino acid sequence of SEQ ID NO: 2, 4, 8 or 10;
   c) a nucleic acid sequence encoding a polypeptide having at least 95% sequence identity to the amino acid sequence of SEQ ID NO: 2, 4, 8 or 10, wherein said-polypeptide has dehydratase activity; and
   d) a nucleic acid sequence which hybridizes to the nucleic acid sequence of a) under stringent conditions comprising hybridization in 6× sodium chloride/sodium citrate (SSC) at approximately 65° C. followed by one or more wash steps in 0.2× SSC, 0.1% SDS at 50 to 65° C. for 15 minutes, wherein said nucleic acid sequence encodes a polypeptide having dehydratase activity.

2. The isolated nucleic acid molecule of claim 1, wherein said nucleic acid sequence encodes a fatty acid dehydratase protein having activity of catalyzing removal of $H_2O$ from a 3-hydroxyacyl fatty acid.

3. The isolated nucleic acid molecule of claim 1, wherein said nucleic acid molecule further comprises a nucleotide sequence encoding a heterologous polypeptide.

4. A vector comprising the isolated nucleic acid molecule of claim 1.

5. The vector of claim 4, which is an expression vector.

6. The nucleic acid molecule of claim 1, wherein the at least one regulatory sequence is a seed-specific promoter.

7. The nucleic acid molecule of claim 6, wherein the seed-specific promoter is selected from the group consisting of Conlinin 1, Conlinin 2, napin, USP, LeB4, Arc, Fae, ACP, LuPXR, SBP and LuFad3.

8. A host cell comprising the isolated nucleic acid molecule of claim 1 or a vector comprising said nucleic acid molecule.

9. The host cell of claim 8, wherein said cell is a plant cell.

10. The host cell of claim 9, wherein said plant cell is a cell obtained from an oilseed crop.

11. The host cell of claim 10, wherein the oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cocoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

12. The host cell of claim 8, wherein said cell is a microbial cell.

13. The host cell of claim 12, wherein the microbial cell is selected from the group consisting of Candida, Cryptococcus, Lipomyces, Rhodosporidium, Yarrowia, Thraustochorium, Pythium, Schizochytrium and Crythecodinium.

14. A plant or plant seed comprising the isolated nucleic acid molecule of claim 1, a vector comprising said nucleic acid molecule, or a host cell comprising said nucleic acid molecule or said vector.

15. A method of producing a polypeptide, comprising culturing the host cell of claim 8 in an appropriate culture medium, and producing a polypeptide encoded by said nucleic acid sequence.

16. A recombinant fusion polypeptide comprising the polypeptide encoded by the isolated nucleic acid molecule of claim 1 fused to a heterologous polypeptide.

17. A method for producing an unsaturated fatty acid, comprising culturing the host cell of claim 8 or a plant or plant seed comprising said host cell such that an unsaturated fatty acid is produced.

18. A method of modulating the production of an unsaturated fatty acid, comprising culturing the host cell of claim 8 or a plant or plant seed comprising said host cell, such that modulation of the production of an unsaturated fatty acid occurs.

19. The method of claim 17, wherein said method further comprises recovering the unsaturated fatty acid from said culture.

20. A method of producing an unsaturated fatty acid comprising contacting a composition comprising at least one dehydratase target molecule with the recombinant polypeptide of claim 16 under conditions such that an unsaturated fatty acid is produced.

21. The method of claim 20, wherein the dehydratase target molecule is 3-hydroxyacyl-ACP or 3-hydroxyacyl-CoA of GLA, DGLA, AA, and eicosapentaenoic acid.

22. A method of producing a host cell, plant or plant seed capable of generating an unsaturated fatty acid, comprising introducing into a host cell, plant or plant seed the isolated nucleic acid molecule of claim 1 or a vector comprising said nucleic acid molecule, and selecting a host cell, plant or plant seed capable of generating an unsaturated fatty acid.

23. The method of claim 17, wherein the unsaturated fatty acid is selected from the group consisting of DGLA, AA, EPA, DPA, and DHA.

24. A cell comprising an isolated nucleic acid molecule selected from the group consisting of:
- a) a nucleic acid molecule comprising the nucleotide sequence of SEQ ID NO: 1, 3, 7 or 9, wherein the nucleic acid molecule is disrupted by at least one technique selected from the group consisting of a point mutation, a truncation, an inversion, a deletion, an addition, a substitution and homologous recombination, and wherein the nucleic acid molecule encodes:
  - i) a polypeptide having at least 95% sequence identity to the amino acid sequence of SEQ ID NO: 2 or 4 and having dehydratase activity; or
  - ii) a polypeptide having at least 80% sequence identity to the amino acid sequence of SEQ ID NO: 8 or 10 and having dehydratase activity; and
- b) a nucleic acid molecule comprising the nucleotide sequence of SEQ ID NO: 1, 3, 7 or 9, wherein the nucleic acid molecule comprises one or more nucleic acid modifications as compared to the sequence set forth in SEQ ID NO: 1, 3, 7 or 9, wherein the modification is selected from the group consisting of a point mutation, a truncation, an inversion, a deletion, an addition and a substitution, and wherein the nucleic acid molecule encodes:
  - i) a polypeptide having at least 95% sequence identity to the amino acid sequence of SEQ ID NO: 2 or 4 and having dehydratase activity; or
  - ii) a polypeptide having at least 80% sequence identity to the amino acid sequence of SEQ ID NO: 8 or 10 and having dehydratase activity.

25. The method of claim 18, wherein said method further comprises recovering the unsaturated fatty acid from said culture.

26. The method of claim 18, wherein the unsaturated fatty acid is selected from the group consisting of DGLA, AA, EPA, DPA, and DHA.

27. The method of claim 21, wherein the unsaturated fatty acid is selected from the group consisting of DGLA, AA, EPA, DPA, and DHA.

28. The method of claim 23, wherein the unsaturated fatty acid is selected from the group consisting of DGLA, AA, EPA, DPA, and DHA.

29. The cell of claim 24, wherein the nucleic acid molecule encodes a polypeptide having at least 95% sequence identity to the amino acid sequence of SEQ ID NO: 2, 4, 8 or 10 and having dehydratase activity.

30. An isolated nucleic acid molecule comprising at least one regulatory sequence operably linked to an heterologous nucleic acid sequence encoding a polypeptide having at least 80% sequence identity to the amino acid sequence of SEQ ID NO: 8 or 10, wherein said polypeptide has dehydratase activity.

* * * * *

SEQUENCE LISTING

```
<160> NUMBER OF SEQ ID NOS: 17

<210> SEQ ID NO 1
<211> LENGTH: 677
<212> TYPE: DNA
<213> ORGANISM: Brassica napus

<400> SEQUENCE: 1
gttagtacat ggcggggtct ttctccttcg tccgtcgcgt gtacctcact ctctacaatt      60
ggatcgtctt tgcaggatgg gatcaagttc tgtactttgc ggtaaagacg ttgaaggaaa     120
gtggacatga aaatgtgtat gacgccgtcg agaagcctct ccagcttgct cagaccgccg     180
ccgttctcga gattctacat ggactagttg gtttggttag atctcctgtt tcagcaactc     240
```

-continued

```
tgccgcagat aggttcaagg ctgtttctca cttggggaat cctatacagc tttccagagg   300
tccagacaca ttttcttgtt gcttcgctgg tcataagctg gtctatcacc gagattattc   360
gctactcctt ctttggtctt aaggaagctt taggctttgc accttcatgg cacttgtggc   420
tcagatacag cagctttta gtgctgtacc cgaccggtat caccagtgaa gtaggtctta    480
tctaccttgc gttaccacac atcaagacgt ctgagatgta cagcgttagg atgccaaaca   540
cattgaactt ctcattcgac ttcttctacg caacgatact cgcccttgca atatatgtcc   600
caggcagtcc acacatgtac aggtacatgc ttggtcagcg taagagagct ctctccaaat   660
ccaagaggga ataaaaa                                                  677
```

<210> SEQ ID NO 2
<211> LENGTH: 221
<212> TYPE: PRT
<213> ORGANISM: Brassica napus

<400> SEQUENCE: 2

```
Met Ala Gly Ser Phe Ser Phe Val Arg Arg Val Tyr Leu Thr Leu Tyr
1               5                   10                  15

Asn Trp Ile Val Phe Ala Gly Trp Asp Gln Val Leu Tyr Phe Ala Val
            20                  25                  30

Lys Thr Leu Lys Glu Ser Gly His Glu Asn Val Tyr Asp Ala Val Glu
        35                  40                  45

Lys Pro Leu Gln Leu Ala Gln Thr Ala Ala Val Leu Glu Ile Leu His
    50                  55                  60

Gly Leu Val Gly Leu Val Arg Ser Pro Val Ser Ala Thr Leu Pro Gln
65                  70                  75                  80

Ile Gly Ser Arg Leu Phe Leu Thr Trp Gly Ile Leu Tyr Ser Phe Pro
                85                  90                  95

Glu Val Gln Thr His Phe Leu Val Ala Ser Leu Val Ile Ser Trp Ser
            100                 105                 110

Ile Thr Glu Ile Ile Arg Tyr Ser Phe Gly Leu Lys Glu Ala Leu
        115                 120                 125

Gly Phe Ala Pro Ser Trp His Leu Trp Leu Arg Tyr Ser Ser Phe Leu
    130                 135                 140

Val Leu Tyr Pro Thr Gly Ile Thr Ser Glu Val Gly Leu Ile Tyr Leu
145                 150                 155                 160

Ala Leu Pro His Ile Lys Thr Ser Glu Met Tyr Ser Val Arg Met Pro
                165                 170                 175

Asn Thr Leu Asn Phe Ser Phe Asp Phe Phe Tyr Ala Thr Ile Leu Ala
            180                 185                 190

Leu Ala Ile Tyr Val Pro Gly Ser Pro His Met Tyr Arg Tyr Met Leu
        195                 200                 205

Gly Gln Arg Lys Arg Ala Leu Ser Lys Ser Lys Arg Glu
    210                 215                 220
```

<210> SEQ ID NO 3
<211> LENGTH: 677
<212> TYPE: DNA
<213> ORGANISM: Brassica napus

<400> SEQUENCE: 3

```
gttagtacat ggcggggtct ttctccttcg ttcgtcgcgt gtacctcact ctctacaatt    60
ggatcgtctt tgcaggatgg gctcaagttc tgtactttgc ggtaaagacg ttgaaggaaa   120
ctggacatga acatgtctat gacgctgtgg agaagcctct ccagcttgct cagaccgccg   180
```

```
ccgttctcga gattcttcat ggattagtag gtttggtcag atctcctgtc tctgctactc    240
tgccgcagat aggttcaagg ctgtttctga cttggggcat cctatacagc tttccagagg    300
tccagtcaca ttttcttgtt gcgtcgctgg tcataagctg gtctatcacg gagattattc    360
gctactcctt ctttggtctc aaggaagctc taggctttgc accttcatgg cacttgtggc    420
tcagatacag cagcttttta gtgctatatc caaccggtat caccagtgaa gtaggtctta    480
tctaccttgc gttaccacac atcaagacgt ctgagatgta cagtgttagg atgcctaaca    540
cattgaactt ctcattcgac ttcttctacg caacgttact cgtccttgca atatatgtcc    600
caggcagtcc acacatgtac aggtacatgc ttggtcagcg taagagagct ctctccaaat    660
ccaagaggga ataaaaa                                                    677
```

<210> SEQ ID NO 4
<211> LENGTH: 221
<212> TYPE: PRT
<213> ORGANISM: Brassica napus

<400> SEQUENCE: 4

```
Met Ala Gly Ser Phe Ser Phe Val Arg Arg Val Tyr Leu Thr Leu Tyr
1               5                   10                  15

Asn Trp Ile Val Phe Ala Gly Trp Ala Gln Val Leu Tyr Phe Ala Val
            20                  25                  30

Lys Thr Leu Lys Glu Thr Gly His Glu His Val Tyr Asp Ala Val Glu
        35                  40                  45

Lys Pro Leu Gln Leu Ala Gln Thr Ala Ala Val Leu Glu Ile Leu His
    50                  55                  60

Gly Leu Val Gly Leu Val Arg Ser Pro Val Ser Ala Thr Leu Pro Gln
65                  70                  75                  80

Ile Gly Ser Arg Leu Phe Leu Thr Trp Gly Ile Leu Tyr Ser Phe Pro
                85                  90                  95

Glu Val Gln Ser His Phe Leu Val Ala Ser Leu Val Ile Ser Trp Ser
            100                 105                 110

Ile Thr Glu Ile Ile Arg Tyr Ser Phe Phe Gly Leu Lys Glu Ala Leu
        115                 120                 125

Gly Phe Ala Pro Ser Trp His Leu Trp Leu Arg Tyr Ser Ser Phe Leu
    130                 135                 140

Val Leu Tyr Pro Thr Gly Ile Thr Ser Glu Val Gly Leu Ile Tyr Leu
145                 150                 155                 160

Ala Leu Pro His Ile Lys Thr Ser Glu Met Tyr Ser Val Arg Met Pro
                165                 170                 175

Asn Thr Leu Asn Phe Ser Phe Asp Phe Phe Tyr Ala Thr Leu Leu Val
            180                 185                 190

Leu Ala Ile Tyr Val Pro Gly Ser Pro His Met Tyr Arg Tyr Met Leu
        195                 200                 205

Gly Gln Arg Lys Arg Ala Leu Ser Lys Ser Lys Arg Glu
    210                 215                 220
```

<210> SEQ ID NO 5
<211> LENGTH: 655
<212> TYPE: DNA
<213> ORGANISM: Euglena gracilis

<400> SEQUENCE: 5

```
ggaacatgta caacgctggc caagctggcg gttggatgat tgccctgggg aagatcctgg    60
```

```
ctcatgccgc ctccggcaac aagtcctccc tgtggggagc ggtggggccg accatcagca      120
agttccagtg ctggccgtt ctggaggtgg tccacgccgc cctcggcatg gtgcggtccc       180
ccgtggcaac caccttcatg caggtcctgt cgcgcgtgat gctggtgagt gccgtccagt      240
acgccccgtc cacccagggc aacgacaact ggttcttgtg gctgatgtgc ctggcctgga      300
gcatcaccga agtggtgcgg tacagctact acagcctgag ccagcagggg gtcaatgaca      360
agctgctcac gtggttgcgg tacagccgt tcgtggtgct gtaccctgcc ggggtggccg       420
gggaaatggg ctgcctgtac aagtccatcc ccgccatgaa ggacaccccc ccggcagacg      480 ccccttcct tgtgaagcac atgctgcagc caatgctgaa gaattccctg ggtaccctgc       540
tcatcgttgt gccggtttat gttgttgggc tgaaaactct gtattcatac atgctggcac      600
agcgccgaaa aatctttggt ggtgccgaga agaagaatca atgacacaag cttgg           655
```

<210> SEQ ID NO 6
<211> LENGTH: 212
<212> TYPE: PRT
<213> ORGANISM: Euglena gracilis

<400> SEQUENCE: 6

```
Met Tyr Asn Ala Gly Gln Ala Gly Gly Trp Met Ile Ala Leu Gly Lys
1               5                   10                  15

Ile Leu Ala His Ala Ala Ser Gly Asn Lys Ser Ser Leu Trp Gly Ala
            20                  25                  30

Val Gly Pro Thr Ile Ser Lys Phe Gln Trp Leu Ala Val Leu Glu Val
        35                  40                  45

Val His Ala Ala Leu Gly Met Val Arg Ser Pro Val Ala Thr Thr Phe
    50                  55                  60

Met Gln Val Leu Ser Arg Val Met Leu Val Ser Ala Val Gln Tyr Ala
65                  70                  75                  80

Pro Ser Thr Gln Gly Asn Asp Asn Trp Phe Leu Trp Leu Met Cys Leu
                85                  90                  95

Ala Trp Ser Ile Thr Glu Val Val Arg Tyr Ser Tyr Tyr Ser Leu Ser
            100                 105                 110

Gln Gln Gly Val Asn Asp Lys Leu Leu Thr Trp Leu Arg Tyr Ser Leu
        115                 120                 125

Phe Val Val Leu Tyr Pro Ala Gly Val Ala Gly Glu Met Gly Cys Leu
    130                 135                 140

Tyr Lys Ser Ile Pro Ala Met Lys Asp Thr Pro Pro Ala Asp Ala Pro
145                 150                 155                 160

Phe Leu Val Lys His Met Leu Gln Pro Met Leu Lys Asn Ser Leu Gly
                165                 170                 175

Tyr Leu Leu Ile Val Val Pro Val Tyr Val Val Gly Leu Lys Thr Leu
            180                 185                 190

Tyr Ser Tyr Met Leu Ala Gln Arg Arg Lys Ile Phe Gly Gly Ala Glu
        195                 200                 205

Lys Lys Asn Gln
    210
```

<210> SEQ ID NO 7
<211> LENGTH: 697
<212> TYPE: DNA
<213> ORGANISM: Euglena gracilis

<400> SEQUENCE: 7

```
ggaacatggc ggttttcacc aactacgtcc taaagacgta tctcacgatg tacaacgctg       60
```

```
gccaagctgg cggttggatg attgccctgg ggaagatcct ggctcatgcc gcctccggca    120
acaagtcctc cctgtgggga gcggtggggc cgaccatcag caagttccag tggctggccg    180
ttctggaggt ggtccacgcc gccctcggca tggtgcggtc cccgtggca accaccttca     240 tgcaggtcct gtcgcgcgtg atgctggtga gtgccgtcca gtacgcccg tccacccagg     300 gcaacgacaa ctggttcttg tggctgatgt gcctggcctg gagcatcacc gaagtggtgc    360
ggtacagcta ctacagcctg agccagcagg gggtcaatga caagctgctc acgtggttgc    420
ggtacagcct gttcgtggtg ctgtaccctg ccggggtggc cggggaaatg ggctgcctgt    480
acaagtccat ccccgccatg aaggacaccc cccggcaga cgcccccttc cttgtgaagc     540
acatgctgca gccaatgctg aagaattccc tggggtacct gctcatcgtt gtgccggttt    600
atgttgttgg gctgaaaact ctgtattcat acatgctggc acagcgccga aaaatctttg    660
gtggtgccga aagaagaat caatgacaca agcttgg                              697

<210> SEQ ID NO 8
<211> LENGTH: 226
<212> TYPE: PRT
<213> ORGANISM: Euglena gracilis

<400> SEQUENCE: 8

Met Ala Val Phe Thr Asn Tyr Val Leu Lys Thr Tyr Leu Thr Met Tyr
1               5                   10                  15

Asn Ala Gly Gln Ala Gly Gly Trp Met Ile Ala Leu Gly Lys Ile Leu
                20                  25                  30

Ala His Ala Ala Ser Gly Asn Lys Ser Ser Leu Trp Gly Ala Val Gly
            35                  40                  45

Pro Thr Ile Ser Lys Phe Gln Trp Leu Ala Val Leu Glu Val Val His
        50                  55                  60

Ala Ala Leu Gly Met Val Arg Ser Pro Val Ala Thr Thr Phe Met Gln
65                  70                  75                  80

Val Leu Ser Arg Val Met Leu Val Ser Ala Val Gln Tyr Ala Pro Ser
                85                  90                  95

Thr Gln Gly Asn Asp Asn Trp Phe Leu Trp Leu Met Cys Leu Ala Trp
            100                 105                 110

Ser Ile Thr Glu Val Val Arg Tyr Ser Tyr Tyr Ser Leu Ser Gln Gln
        115                 120                 125

Gly Val Asn Asp Lys Leu Leu Thr Trp Leu Arg Tyr Ser Leu Phe Val
130                 135                 140

Val Leu Tyr Pro Ala Gly Val Ala Gly Glu Met Gly Cys Leu Tyr Lys
145                 150                 155                 160

Ser Ile Pro Ala Met Lys Asp Thr Pro Ala Asp Ala Pro Phe Leu
                165                 170                 175

Val Lys His Met Leu Gln Pro Met Leu Lys Asn Ser Leu Gly Tyr Leu
            180                 185                 190

Leu Ile Val Val Pro Val Tyr Val Gly Leu Lys Thr Leu Tyr Ser
        195                 200                 205

Tyr Met Leu Ala Gln Arg Arg Lys Ile Phe Gly Gly Ala Glu Lys Lys
    210                 215                 220

Asn Gln
225

<210> SEQ ID NO 9
<211> LENGTH: 913
```

```
<212> TYPE: DNA
<213> ORGANISM: Euglena gracilis

<400> SEQUENCE: 9
ggaacatgca ccactttcgg ccgatcgagg tgtttgagca ggaaacgtcc agcgcggtga      60
tgggcctcct cctgatcaat gacatcaaga acgagaacag tgttgctaat ccagccaccc     120
cactccgcaa tccattgctg ctgttcaccg acacgtcttt ccatggtggg gcctggaggt     180
gtggcttcaa gtttggatcc attggtgtgg ggtccgtcct ctccgcggtt ttcaccaact     240
acgtcctaaa gacgtatctc acgatgtaca acgctggcca agctggcggt tggatgattg     300
ccctggggaa gatcctggct catgccgcct ccggcaacaa gtcctccctg tggggagcgg     360
tggggccgac catcagcaag ttccagtggc tggccgttct ggaggtggtc cacgccgcct     420
tcggcatggt gcggtccccc gtggcaacca ccttcgtgca ggtcctgtcg cgcgtgatgc     480
tggtgagtgc cgtccagtac gccccgtcca cccagggcaa cgacaactgg ttcttgtggc     540
tgatgtgcct ggcctggagc atcaccgaag tggtgcggta cagctactac agcctgagcc     600
agcaggggt caatgacaag ctgctcacgt ggttgcggta cagcctgttc gtggtgctgt     660
acctgccgg ggtggccggg gaaatgggct gcctgtacaa gtccatcccc gccatgaagg     720
acaccccccc ggcagacgcc cccttccttg tgaagcacat gctgcagcca atgctgaaga     780
attccctggg gtacctgctc atcgttgtgc cggtttatgt tgttgggctg aaaactctgt     840
attcatacat gctggcacag cgccgaaaaa tctttggtgg tgccgagaag aagaatcaat     900
gacacaagct tgg                                                        913

<210> SEQ ID NO 10
<211> LENGTH: 298
<212> TYPE: PRT
<213> ORGANISM: Euglena gracilis

<400> SEQUENCE: 10

Met His His Phe Arg Pro Ile Glu Val Phe Glu Gln Glu Thr Ser Ser
1               5                   10                  15

Ala Val Met Gly Leu Leu Ile Asn Asp Ile Lys Asn Glu Asn Ser
            20                  25                  30

Val Ala Asn Pro Ala Thr Pro Leu Arg Asn Pro Leu Leu Phe Thr
        35                  40                  45

Asp Thr Ser Phe His Gly Gly Ala Trp Arg Cys Gly Phe Lys Phe Gly
    50                  55                  60

Ser Ile Gly Val Gly Ser Val Leu Ser Ala Val Phe Thr Asn Tyr Val
65                  70                  75                  80

Leu Lys Thr Tyr Leu Thr Met Tyr Asn Ala Gly Gln Ala Gly Gly Trp
                85                  90                  95

Met Ile Ala Leu Gly Lys Ile Leu Ala His Ala Ala Ser Gly Asn Lys
            100                 105                 110

Ser Ser Leu Trp Gly Ala Val Gly Pro Thr Ile Ser Lys Phe Gln Trp
        115                 120                 125

Leu Ala Val Leu Glu Val Val His Ala Ala Phe Gly Met Val Arg Ser
    130                 135                 140

Pro Val Ala Thr Thr Phe Val Gln Val Leu Ser Arg Val Met Leu Val
145                 150                 155                 160

Ser Ala Val Gln Tyr Ala Pro Ser Thr Gln Gly Asn Asp Asn Trp Phe
                165                 170                 175

Leu Trp Leu Met Cys Leu Ala Trp Ser Ile Thr Glu Val Val Arg Tyr
```

```
            180                 185                 190
Ser Tyr Tyr Ser Leu Ser Gln Gln Gly Val Asn Asp Lys Leu Leu Thr
            195                 200                 205

Trp Leu Arg Tyr Ser Leu Phe Val Leu Tyr Pro Ala Gly Val Ala
        210                 215                 220

Gly Glu Met Gly Cys Leu Tyr Lys Ser Ile Pro Ala Met Lys Asp Thr
225                 230                 235                 240

Pro Pro Ala Asp Ala Pro Phe Leu Val Lys His Met Leu Gln Pro Met
                245                 250                 255

Leu Lys Asn Ser Leu Gly Tyr Leu Leu Ile Val Val Pro Val Tyr Val
            260                 265                 270

Val Gly Leu Lys Thr Leu Tyr Ser Tyr Met Leu Ala Gln Arg Arg Lys
        275                 280                 285

Ile Phe Gly Gly Ala Glu Lys Lys Asn Gln
        290                 295
```

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
gttagtacat ggcggggtct ttctc                                       25

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
tttttattcc ctcttggatt tggag                                       25

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
cggcgctgtg ccagcatgta tg                                          22

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
ggaacatgca ccactttcgg ccg                                         23

<210> SEQ ID NO 15
<211> LENGTH: 30
<212> TYPE: DNA
<213> ORGANISM: Artificial sequence
<220> FEATURE:
<223> OTHER INFORMATION: Primer

```
<400> SEQUENCE: 15
ggaacatggc ggttttcacc aactacgtcc                                            30

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
ggaacatgta caacgctggc caagc                                                 25

<210> SEQ ID NO 17
<211> LENGTH: 31
<212> TYPE: DNA
<213> ORGANISM: Artificial sequence
<220> FEATURE:
<223> OTHER INFORMATION: Primer

<400> SEQUENCE: 17
ccaagcttgt gtcattgatt cttcttctcg g                                          31
```